US008188222B2

(12) United States Patent
Yamamoto et al.

(10) Patent No.: US 8,188,222 B2
(45) Date of Patent: May 29, 2012

(54) HIGH MOLECULAR WEIGHT DERIVATIVE OF NUCLEIC ACID ANTIMETABOLITE

(75) Inventors: Keiichiro Yamamoto, Kita-ku (JP); Kazutoshi Takashio, Kita-ku (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 430 days.

(21) Appl. No.: 12/312,157

(22) PCT Filed: Nov. 6, 2007

(86) PCT No.: PCT/JP2007/071532
§ 371 (c)(1), (2), (4) Date: Jun. 15, 2009

(87) PCT Pub. No.: WO2008/056654
PCT Pub. Date: May 15, 2008

(65) Prior Publication Data
US 2010/0029849 A1  Feb. 4, 2010

(30) Foreign Application Priority Data
Nov. 8, 2006 (JP) .................................. 2006-302686

(51) Int. Cl.
| C07K 5/037 | (2006.01) |
| C07H 19/06 | (2006.01) |
| C07H 19/067 | (2006.01) |
| C07H 19/073 | (2006.01) |
| C07H 19/09 | (2006.01) |
| C07H 19/16 | (2006.01) |
| C07H 19/167 | (2006.01) |
| C07H 19/173 | (2006.01) |
| C07H 19/19 | (2006.01) |
| A61K 31/7068 | (2006.01) |
| A61K 31/7072 | (2006.01) |
| A61K 31/7076 | (2006.01) |
| A61K 31/708 | (2006.01) |
| A61K 38/06 | (2006.01) |
| A61K 38/07 | (2006.01) |
| A61K 38/08 | (2006.01) |
| A61K 38/10 | (2006.01) |
| A61K 38/16 | (2006.01) |

(52) U.S. Cl. ................... 530/332; 536/27.23; 536/27.3; 536/27.6; 536/27.62; 536/27.63; 536/27.81; 536/28.51; 536/28.53; 536/28.54; 536/28.55; 514/45; 514/46; 514/49; 514/50; 514/21.2; 514/21.3; 514/21.4; 514/21.5; 514/21.6; 514/21.7; 514/21.8; 514/21.9

(58) Field of Classification Search .......................... None
See application file for complete search history.

(56) References Cited

U.S. PATENT DOCUMENTS

| 3,979,449 | A | 9/1976 | Hirsbrunner et al. |
| 4,734,512 | A | 3/1988 | Kaneko et al. |
| 5,037,883 | A | 8/1991 | Kopecek et al. |
| 5,412,072 | A | 5/1995 | Sakurai et al. ................. 530/322 |
| 5,438,072 | A | 8/1995 | Bobee et al. |
| 5,571,889 | A | 11/1996 | Katoh et al. .................. 528/328 |
| 5,614,549 | A | 3/1997 | Greenwald et al. |
| 5,877,205 | A | 3/1999 | Andersson |
| 6,025,385 | A | 2/2000 | Shimizu et al. |
| 6,153,655 | A | 11/2000 | Martinez et al. |
| 6,262,107 | B1 | 7/2001 | Li et al. |
| 6,322,817 | B1 | 11/2001 | Maitra et al. |
| 6,376,470 | B1 | 4/2002 | Greenwald et al. |
| 6,410,731 | B2 | 6/2002 | Curran et al. |
| 6,458,347 | B1 | 10/2002 | Sugawara et al. |
| 6,596,757 | B1 | 7/2003 | Chari et al. |
| 6,713,454 | B1 | 3/2004 | Ekwuribe et al. |
| 6,720,306 | B2 | 4/2004 | Greenwald et al. |
| 7,138,490 | B2 | 11/2006 | Nakanishi et al. |
| 7,495,099 | B2 | 2/2009 | Kitagawa et al. |
| 7,700,709 | B2 | 4/2010 | Masuda et al. |
| 7,820,759 | B2 | 10/2010 | Shimizu et al. |
| 2001/0003779 | A1 | 6/2001 | Curran et al. |
| 2001/0014354 | A1 | 8/2001 | Yokoyama et al. |
| 2001/0041189 | A1 | 11/2001 | Xu |
| 2002/0016285 | A1 | 2/2002 | Bhatt et al. ........................ 514/2 |
| 2002/0099013 | A1 | 7/2002 | Piccariello et al. ............. 514/12 |
| 2002/0119951 | A1 | 8/2002 | Seyedi et al. |
| 2002/0161062 | A1 | 10/2002 | Biermann et al. |

(Continued)

FOREIGN PATENT DOCUMENTS

CA  2 383 240 A1  3/2001

(Continued)

OTHER PUBLICATIONS

Chinese Office Action dated Nov. 10, 2010 in co-pending U.S. Appl. No. 12/309,061, filed Mar. 3, 2009 Foreign Application No. 200780027210.8.

(Continued)

Primary Examiner — Eric S Olson
(74) Attorney, Agent, or Firm — Nields, Lemack & Frame, LLC

(57) ABSTRACT

[Problems] A derivative of a nucleic acid antimetabolite is demanded which can show a higher therapeutic effect at a lower dose.

[Means for Solving Problems] Disclosed is a high molecular weight derivative a nucleic acid antimetabolite, which is characterized by comprising a high molecular weight compound comprising a polyethylene glycol moiety and a polymer moiety having a carboxyl group in a side chain and a nucleoside derivative which can act as a nucleic acid antimetabolite, wherein the nucleoside derivative is bound to the carboxyl group in the side chain of the high molecular weight compound via a highly hydrophobic linker.

18 Claims, 1 Drawing Sheet

U.S. PATENT DOCUMENTS

| | | | |
|---|---|---|---|
| 2002/0183259 A1 | 12/2002 | Choe et al. | 514/19 |
| 2003/0032593 A1 | 2/2003 | Wender et al. | |
| 2003/0054977 A1* | 3/2003 | Kumar et al. | 514/2 |
| 2003/0149003 A1 | 8/2003 | Chaplin et al. | |
| 2005/0119193 A1 | 6/2005 | Motoyama | |
| 2005/0147617 A1 | 7/2005 | Ji et al. | 424/178.1 |
| 2006/0057219 A1 | 3/2006 | Nagasaki et al. | |
| 2006/0067910 A1 | 3/2006 | Kitagawa et al. | 424/78.36 |
| 2006/0099265 A1 | 5/2006 | Shimizu et al. | |
| 2006/0233883 A1 | 10/2006 | Ishihara et al. | |
| 2007/0004674 A1 | 1/2007 | Shiotsu et al. | |
| 2008/0113028 A1 | 5/2008 | Shimizu et al. | |
| 2008/0145432 A1 | 6/2008 | Kakizawa et al. | |
| 2008/0221062 A1 | 9/2008 | Miyamoto et al. | |
| 2008/0269218 A1 | 10/2008 | Kuramochi et al. | |
| 2008/0280937 A1 | 11/2008 | Leamon et al. | |
| 2009/0012252 A1 | 1/2009 | Masuda et al. | |
| 2009/0162313 A1 | 6/2009 | Kitagawa et al. | |
| 2009/0239782 A1 | 9/2009 | Nakamura et al. | |
| 2009/0275732 A1 | 11/2009 | Hirotsu et al. | |
| 2009/0281300 A1 | 11/2009 | Yamamoto et al. | |
| 2010/0004403 A1 | 1/2010 | Kitagawa et al. | |
| 2010/0234537 A1 | 9/2010 | Kitagawa et al. | |
| 2010/0292414 A1 | 11/2010 | Kitagawa et al. | |
| 2011/0201754 A1 | 8/2011 | Kitagawa | |
| 2011/0294980 A1 | 12/2011 | Nakanishi | |

FOREIGN PATENT DOCUMENTS

| | | |
|---|---|---|
| CA | 2 334 615 A1 | 8/2001 |
| CN | 1307866 A | 8/2001 |
| CN | 1708540 A | 12/2005 |
| EP | 0 397 307 A2 | 11/1990 |
| EP | 0 583 955 A2 | 2/1994 |
| EP | 0 757 049 A1 | 2/1997 |
| EP | 1 127 570 A2 | 8/2001 |
| EP | 1 857 446 A1 | 11/2007 |
| JP | 61-243026 A | 10/1986 |
| JP | 62-96088 A | 5/1987 |
| JP | 62-145093 A | 6/1987 |
| JP | 63-10789 A | 1/1988 |
| JP | 63-23884 A | 2/1988 |
| JP | 64-61422 A | 3/1989 |
| JP | 64-61423 A | 3/1989 |
| JP | 2-300133 | 12/1990 |
| JP | 5-955 | 1/1993 |
| JP | 5-117385 A | 5/1993 |
| JP | 6-107565 A | 4/1994 |
| JP | 6-206815 A | 7/1994 |
| JP | 6-206830 A | 7/1994 |
| JP | 6-206832 | 7/1994 |
| JP | 6-296088 A | 10/1994 |
| JP | 6-310789 A | 11/1994 |
| JP | 6-323884 A | 11/1994 |
| JP | 8-48766 | 2/1996 |
| JP | 8-503689 A | 4/1996 |
| JP | 8-310970 A | 11/1996 |
| JP | 2694923 | 9/1997 |
| JP | 10-513187 A | 12/1998 |
| JP | 11-335267 A | 12/1999 |
| JP | 2000-515132 A | 11/2000 |
| JP | 2000-516948 A | 12/2000 |
| JP | 2000-517304 A | 12/2000 |
| JP | 2001-226294 A | 8/2001 |
| JP | 3268913 | 1/2002 |
| JP | 2002-508400 A | 3/2002 |
| JP | 2002-512265 A | 4/2002 |
| JP | 3310000 A | 5/2002 |
| JP | 2003-509385 A | 3/2003 |
| JP | 2003-509386 A | 3/2003 |
| JP | 2003-511349 A | 3/2003 |
| JP | 2003-511423 A | 3/2003 |
| JP | 2003-524028 | 8/2003 |
| JP | 2003-525238 A | 8/2003 |
| JP | 2003-527443 | 9/2003 |
| JP | 2003-342167 A | 12/2003 |
| JP | 2003-342168 A | 12/2003 |
| JP | 2003-342269 A | 12/2003 |
| JP | 2004-39869 A | 2/2004 |
| JP | 2004-530736 A | 10/2004 |
| JP | 2004-532289 | 10/2004 |
| JP | 2005-507912 A | 3/2005 |
| JP | 2005-508832 A | 4/2005 |
| JP | 2005-517675 A | 6/2005 |
| JP | 2005-519122 | 6/2005 |
| JP | 2005-533026 A | 11/2005 |
| JP | 2006-510627 A | 3/2006 |
| JP | 2006-511571 A | 4/2006 |
| JP | 2006-120914 A | 5/2006 |
| JP | 2006-517572 A | 7/2006 |
| JP | 2006-524673 A | 11/2006 |
| JP | 2007-111211 A | 5/2007 |
| JP | 2008-41610 A | 2/2008 |
| JP | 2006-521367 A | 10/2010 |
| WO | 93/24476 A | 12/1993 |
| WO | 96/23794 A | 8/1996 |
| WO | 97/38727 A | 10/1997 |
| WO | 98/02426 A | 1/1998 |
| WO | 98/07713 A | 2/1998 |
| WO | 98/08489 A1 | 3/1998 |
| WO | 99/53951 A | 10/1999 |
| WO | 01/19361 A2 | 3/2001 |
| WO | 01/19406 A2 | 3/2001 |
| WO | 01/19407 A2 | 3/2001 |
| WO | 01/26693 A2 | 4/2001 |
| WO | 01/64198 A2 | 9/2001 |
| WO | 01/70275 A2 | 9/2001 |
| WO | 01/92584 A1 | 12/2001 |
| WO | 02/06279 A1 | 1/2002 |
| WO | 02/065986 A2 | 8/2002 |
| WO | 02/065988 A2 | 8/2002 |
| WO | 02/066066 A1 | 8/2002 |
| WO | 03/000771 A1 | 1/2003 |
| WO | 03/035008 A2 | 5/2003 |
| WO | 03/055860 A1 | 7/2003 |
| WO | 2004/039869 | 5/2004 |
| WO | 2004/050087 A1 | 6/2004 |
| WO | 2004/056782 A1 | 7/2004 |
| WO | 2004/072051 A1 | 8/2004 |
| WO | 2004/082718 A1 | 9/2004 |
| WO | 2004/096212 A1 | 11/2004 |
| WO | 2005/000300 A1 | 1/2005 |
| WO | 2005/018674 A1 | 3/2005 |
| WO | 2005/066214 A1 | 7/2005 |
| WO | 2006/055760 A1 | 5/2006 |
| WO | 2006/095668 A1 | 9/2006 |
| WO | 2006/095783 A1 | 9/2006 |
| WO | 2006/115293 A1 | 11/2006 |
| WO | 2006/120914 | 11/2006 |
| WO | 2007/022493 A2 | 2/2007 |
| WO | 2007/080898 A1 | 7/2007 |
| WO | 2007/111211 | 10/2007 |
| WO | 2007/135910 A1 | 11/2007 |
| WO | 2008/010463 A1 | 1/2008 |
| WO | 2008/041610 | 4/2008 |
| WO | 2008/056596 A1 | 5/2008 |

OTHER PUBLICATIONS

Korean Office Action dated Nov. 8, 2010 in co-pending U.S. Appl. No. 10/548,998, filed Oct. 31, 2005 Foreign Application No. 10-2005-7017245.

Bioorganic & Medicinal Chemistry Letters 15 (2005) pp. 3338-3343, "The identification, synthesis, protein crystal structure and in vitro biochemical evaluation of a new 3,4-diarylpyrazole class of Hsp90 inhibitors", Cheung, et al.

Molecular Cancer Therapeutics, 2006, 5(6), Jun. 2006, pp. 1628-1637, "Preclinical pharmacokinetics and metabolism of a novel diaryl pyrazole resorcinol series of heat shock protein 90 inhibitors", Smith, et al.

Registry Entry for Registry No. 171009-07-7, which entered STN on Dec. 6, 1995, 3 pages.

Registry Entry for Registry No. 7689-03-4, which entered STN on Nov. 16, 1984, 3 pages.

Merriam-Webster Online Dictionary entry for "Derivative", (http://www.merriam-webster.com/dictionary/derivative), last accessed Feb. 9, 2011, 3 pages.

Office Action dated Apr. 4, 2011 in co-pending U.S. Appl. No. 12/311,086.
Final Rejection dated Feb. 28, 2011 in co-pending U.S. Appl. No. 12/309,061.
Cancer Sci; Feb. 2004; vol. 95; No. 2;pp. 105-111; Akira Matsuda et al.; "Antitumor Activity of Sugar-Modified Cytosine Nucleosides".
Cancer Research 44, pp. 25-30, Jan. 1984; Yoshinori Kato et al.; "Antitumor Activity of 1-β-D-Arabinofuranosylcytosine conjugated With Polyglutamic Acid and Its Derivative".
Journal of Controlled Release 79 (2002) p. 55-70; Yun H. Choe et al.; "Anticancer drug delivery systems: multi-loaded N4-acyl poly(ethylene glycol) prodrugs of ara-C. II. Efficacy in ascites and solid tumors".
International Search Report dated Jan. 29, 2008 (U.S. Appl. No. 12/312,009).
Final Rejection dated Jun. 8, 2011 in co-pending U.S. Appl. No. 11/662,834.
Office Action dated Jun. 16, 2011 in co-pending U.S. Appl. No. 12/225,230.
Final Rejection dated Jul. 27, 2011 in co-pending U.S. Appl. No. 12/311,086.
Russian Communication, with English translation, dated May 16, 2011 in co-pending foreign patent application No. RU 2008149932/04.
International Search Report dated Dec. 24, 2003 in U.S. patent 7,495,099 (PCT/JP03/13838).
Taiwanese communication dated Nov. 30, 2006 in U.S. patent 7,495,099 (TW092130275).
Russian communication dated Apr. 20, 2007 in U.S. patent 7,495,099 (RU2005116309/04).
European communication dated Sep. 25, 2008 in U.S. patent 7,495,099 (EP03769949.3).
International Search Report dated May 11, 2004 in co-pending U.S. Appl. No. 10/548,998 (PCT/JP2004/003647).
Chinese communication dated Oct. 20, 2006 in co-pending U.S. Appl. No. 10/548,998 (CN200480007329.5).
Russian communication dated Jun. 27, 2007 in co-pending U.S. Appl. No. 10/548,998 (RU2005132309/04).
European communication dated Feb. 17, 2009 in co-pending U.S. Appl. No. 10/548,998 (EP04721673.4).
Chinese communication dated Apr. 17, 2009 in co-pending U.S. Appl. No. 10/548,998 (CN200480007329.5).
European communication dated Jun. 5, 2009 in co-pending U.S. Appl. No. 10/548,998 (EP04721673.4).
International Search Report dated Nov. 15, 2005 in co-pending U.S. Appl. No. 12/322,322 (PCT/JP2005/017127).
International Search Report dated Jul. 25, 2006 in U.S. Patent 7,700,709 (PCT/JP2006/308826).
International Search Report dated May 15, 2007 in co-pending U.S. Appl. No. 12/225,230 (PCT/JP2007/055809).
International Search Report dated Aug. 21, 2007 in co-pending U.S. Appl. No. 12/226,962 (PCT/JP2007/060026).
European communication dated Oct. 23, 2009 in co-pending U.S. Appl. No. 12/226,962 (EP07743461.1).
International Search Report dated Oct. 16, 2007 in co-pending U.S. Appl. No. 12/309,061 (PCT/JP2007/063990).
International Search Report dated Jan. 8, 2008 in co-pending U.S. Appl. No. 12/311,086 (PCT/JP2007/068841).
Office Actions dated Jan. 21, 2009, Apr. 17, 2009, Jul. 10, 2009, Mar. 4, 2010 in co-pending U.S. Appl. No. 10/548,998.
Office Actions dated Oct. 19, 2009, Mar. 19, 2010, Jun. 23, 2010, Jul. 7, 2010 in co-pending U.S. Appl. No. 12/322,322.
Office Action dated Aug. 24, 2010 in co-pending U.S. Appl. No. 11/662,834.
Office Actions dated Jul. 21, 2010 in co-pending U.S. Appl. No. 12/309,061.
A.V. Shur, "High-Molecular Weight Compounds"; Course for Universities, Third Edition, Revised and supplemented, "Visshaja Shkola" Publishing House, 1981, 656 pages, see p. 265).
Chemical Abstracts, 6001, vol. 132; Oct. 10, 2000 No. 2—XP-002168038.
Merriam-Webster's Collegiate Dictionary—Eleventh Edition 2004.
J. Org. Chem. 2001, 66, 8135-8138; Keirs Gaukroger, et al.; "Novel Synthesis of Cis and Trans Isomers of Combretastatin A-4".
Anti-Cancer Drug Design; vol. 14, No. 6, Dec. 1999—ISSN 0266-9536.
Journal of Pharmaceutical Sciences, vol. 92, No. 7, Jul. 2003; Monica L. Adams et al.; "MiniReview—Amphiphilic Block Copolymers for Drug Delivery".
Chemistry and Biology, vol. 11, 787-797, Jun. 2004; Maria Vilenchick et al.; "Targeting Wide-Range Oncogenic Transformation via PU24FCl, a specific Inhibitor of Tumor Hsp90".
Trends in Molecular Medicine vol. 8, No. 4 (Suppl.) 2002; Len Neckers; "Hsp90 inhibitors as novel cancer chemotherapeutic agents".
Current Cancer Drug Targets, 2003, 3, 385-390; Udai Banerji et al.; "The Clinical Applications of Heat Shock Protein Inhibitors in Cancer Present and Future".
Journal of Pharmacokinetics and Biopharmaceutics, vol. 23, No. 4, 1995; Claudia S. Leopold; In vivo Pharmacokinetic Study for the Assessment of Poly(L-Aspartic Acid) as a Drug Carrier for Colon-Specific Drug Delivery).
International Search Report dated Dec. 9, 2008 in co-pending U.S. Appl. No. 12/678,620 (PCT/JP2008/067413).
Advanced Drug Delivery Reviews 20 (1996) 1995-201; K. Yokoyama et al; "Limethason as a lipid microsphere preparation: An overview".
Chinese communication dated Aug. 11, 2010 in a co-pending foreign application (CN2007800177809).
Office Action dated Nov. 12, 2010 in a co-pending U.S. Appl. No. 11/662,834.
Journal of Peptide Science, vol. 3, 141-144 (1997); Jan lzdebski et al.; "Evaluation of Carbodiimides Using A Competition Method".
Chinese Communication, with English translation, dated Oct. 10, 2011 in co-pending Chinese Patent Application No. 200880109404.7.
Office Action dated Dec. 15, 2011 in co-pending U.S. Appl. No. 11/662,834.
European Communication, dated Oct. 28, 2011 in co-pending European Patent Application No. EP 05783310.5.
Australian Communication, dated Oct. 28, 2011 in co-pending Australian Patent Application No. 2007252678.
Office Action dated Sep. 9, 2011 in co-pending U.S. Appl. No. 12/226,962.
Colloids and Surfaces B: Biointerfaces V. 16 (1999) pp. 217-226, "Micelle-like structures of poly(ethyleneoxide)-block-poly(2-hydroxyethyl aspartamide)-methotrexate conjugates", Li, et al.
Pharmaceutical Research, V. 17, No. 5 (2000), pp. 607-611, "Methotrexate Esters of Poly (EthyleneOxide)-Block-Poly (2-Hydroxyethyl-L-Aspartamide). Part I: Effects of the Level of Methotrexate Conjugation on the Stability of Micelles and on Drug Release", Li, et al.
International Search Report dated Jul. 21, 2009 in co-pending international patent application No. PCT/JP2009/058325.
Taiwan Communication, with English translation, dated Jul. 22, 2011 in co-pending Taiwan Patent Application No. 094132581.
Office Action mailed Oct. 25, 2011 in co-pending U.S. Appl. No. 12/312,009.
Final Rejection mailed Nov. 8, 2011 in co-pending U.S. Appl. No. 12/225,230.
Chinese Communication, with English translation, dated Sep. 23, 2011 in co-pending Chinese patent application No. 2007800177809.
Journal of Controlled Release, 2001, V. 74, No. 1-3, pp. 295-302, paragraph of "2. Structure of NK911", "Development of the polymer micelle carrier system for doxorubicin", Nakanishi, et al.
International Search Report mailed Jun. 23, 2009 in co-pending PCT application No. PCT/JP2009/055115.
Chinese Communication, with English translation, dated Aug. 31, 2011 in co-pending Chinese patent application No. 200980110087.5.
Taiwanese Communication, with English translation, dated Dec. 14, 2011 in co-pending Taiwanese Application No. 094132581.
Final Rejection dated Feb. 16, 2012 in co-pending U.S. Appl. No. 12/226,962.
Office Action dated Feb. 21, 2012 in co-pending U.S. Appl. No. 12/312,009.

* cited by examiner

HIGH MOLECULAR WEIGHT DERIVATIVE OF NUCLEIC ACID ANTIMETABOLITE

This application is the national stage (§371) of PCT/JP2007/071532, filed Nov. 6, 2007, which claims priority of JP2006-302686, filed Nov. 8, 2006.

TECHNICAL FIELD

The present invention relates to a high molecular weight derivative of a nucleic acid antimetabolite, the uses of the same, and a method for manufacturing the same.

BACKGROUND ART

For the purpose of treating malignant tumors or viral diseases, various nucleic acid antimetabolites has been developed, and, cytarabine, gemcitabine, doxifluridine, azacitidine, decitabine, nelarabine and the like as antitumor agents (anticancer agents), and, zalcitabine, lamivudine and the like as antiviral agents are clinically used.

However, even though these nucleic acid antimetabolites exhibit strong in vitro activity, many of the antimetabolites cannot sufficiently exhibit the efficacy inherently possessed by the drugs, or need to be administered in large amounts, owing to their susceptibility to in vivo metabolization and excretion. For example, gemcitabine has a strong in vitro cell growth inhibitory activity which is comparable to that of anticancer agents such as paclitaxel or doxorubicin, while in clinical practice, gemcitabine needs to be administered at a high does of 1000 mg/m$^2$ of the body surface area per administration. This is considered to be due to a decreased in vivo bioavailability owing to the metabolism/deactivation of the amino group at the 4-position of the base by a cytidine deaminase, which is a 2'-deoxycytidine metabolizing enzyme (see Non-Patent Document 1).

There are some cases where binding of a drug to a polymer results in an improvement in the pharmacokinetics in vivo, and thus to an enhancement of the therapeutic effect. Non-Patent Document 2 describes a high molecular weight derivative in which a polyglutamic acid having an average molecular weight of about 30,000 is conjugated with cytarabine. However, high molecular weight derivatives of drugs sometimes induce hypersensitivity due to immune responses, and in such cases, the high molecular weight derivatives as a drug cannot be administered repeatedly.

Patent Document 1 describes a high molecular weight derivative in which a cytidine derivative is bound to a polyethylene glycol, while Non-Patent Document 3 describes a high molecular weight derivative in which both ends of the chain of a polyethylene glycol are substituted with aspartic acid in a branched form, and cytarabine is bound thereto. Furthermore, Patent Document 6 describes a high molecular weight derivative having a structure in which the ends of a polyethylene glycol chain are branched by making use of amino acids, and each of the branches releases drug after being subjected to a benzyl elimination reaction. However, for all of these high molecular weight derivatives, the rate of hydrolysis in the blood plasma is not so much slowed, being several tens of hours at the most, and the high molecular weight derivatives themselves do not remain in vivo for a long time to release the included compounds over a long time. Also, since these high molecular weight derivatives have large differences between the rate of hydrolysis in phosphate buffered physiological saline (PBS) and the rate of hydrolysis in the blood plasma, and the hydrolysis reaction depends largely on the enzymes in vivo, it is possible that the therapeutic effects in the clinical practice may be greatly affected by the individual differences of patients.

Patent Document 2 describes that molecules in which a drug is bound to a block type polymer having a polyethylene glycol condensed with polyaspartic acid, form micelles and serve as a medicine. Furthermore, Patent Document 3 describes a polymer carrier which serves as a polymer vehicle, in which a hydrophobic substance is bound to a carboxyl group in the side chain of a block copolymer of a polyethylene glycol and a poly acidic amino acid. Furthermore, Patent Document 4 states a polymer in which an anticancerous substance is bound to a carboxyl group in the glutamic acid side chain of a block type polymer having a polyethylene glycol condensed with polyglutamic acid. However, there is no description with regard to these high molecular weight derivatives using a nucleic acid antimetabolite as the drug binding thereto.

Patent Document 5 states that water-soluble high molecular weight derivatives in which a carboxyl group of a polymer of polyethylene glycol and polycarboxylic acid is linked to a phenolic hydroxyl group of a phenolic camptothecin by ester condensation, are suitable for cancer chemotherapy. However, these polymers have a drug bound directly to a carboxyl group of a polymer of polyethylene glycol and polycarboxylic acid, and thus the drug is not linked via any linker. Also, there is no description with regard to a nucleic acid antimetabolite as the drug binding thereto.

Patent Document 1: Japanese Patent Application Laid-Open Publication (Kohyo) No. 2003-524028
Patent Document 2: Japanese Patent No. 2694923
Patent Document 3: Japanese Patent No. 3268913
Patent Document 4: Japanese Patent Application Laid-Open Publication (Kokai) No. 5-955
Patent Document 5: WO 2004/039869
Patent Document 6: Japanese Patent Application Laid-Open Publication (Kohyo) No. 2004-532289
Non-Patent Document 1: Cancer Science, Japanese Cancer Association, Vol. 95, pp. 105-111 (2004)
Non-Patent Document 2: Cancer Research, American Association for Cancer Research, Vol. 44, pp. 25-30 (1984)
Non-Patent Document 3: Journal of Controlled Release, Elsevier, Vol. 79, pp. 55-70 (2002)

DISCLOSURE OF THE INVENTION

Problems to be Solved by the Invention

It is an object of the present invention to provide a nucleic acid antimetabolite which has superior effects at lower doses and serves as a novel anticancer agent or antiviral agent.

Means for Solving the Problems

The inventors of the present invention devotedly conducted research to address the above-described problems, and as a result, found a high molecular weight derivative of a nucleic acid antimetabolite, particularly a high molecular weight derivative of a nucleic acid antimetabolite in which the nucleic acid antimetabolite is linked to a carboxyl group in the side chain of a high molecular weight compound comprising a polyethylene glycol moiety and a polymer moiety having a carboxyl group in the side chain via a hydrophobic linker.

Specifically, the present invention relates to the following (1) to (21).

(1) A high molecular weight derivative of a nucleic acid antimetabolite, in which the nucleic acid antimetabolite is linked to a carboxyl group in the side chain of a high molecular weight compound comprising a polyethylene glycol moiety and a polymer moiety having a carboxyl group in the side chain via a hydrophobic linker.

(2) The high molecular weight derivative of a nucleic acid antimetabolite according to (1) above, wherein the polymer moiety having a carboxyl group in the side chain is a polyaspartic acid or polyglutamic acid derivative.

(3) The high molecular weight derivative of a nucleic acid antimetabolite according to (1) or (2) above, wherein the high molecular weight derivative of a nucleic acid antimetabolite in which the polymer moiety having a carboxyl group in the side chain is a polyglutamic acid derivative, is a compound represented by the following formula (1):

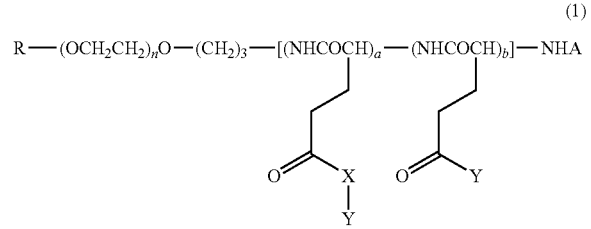

(1)

wherein R represents a hydrogen atom or a C1-C6 alkyl group; A represents a hydrogen atom, a C1-C6 acyl group or a C1-C6 alkoxycarbonyl group; a+b represents from 3 to 200 as an average value, wherein a represents 75 to 100% of a+b, and b represents 0 to 25% of a+b; n represents from 5 to 2000 as an average value; X represents a hydrophobic amino acid residue or a hydrophobic amino acid derivative residue; Y represents two or more groups selected from the group consisting of a nucleic acid antimetabolite residue, a hydroxyl group, and —N(R1)CONH(R2), wherein R1 and R2 may be identical or different, and are each a C1-C6 alkyl group which may be substituted with a tertiary amino group, and wherein, assuming that a+b is 100%, the number of nucleic acid antimetabolite residue is 5 to 80%, the number of —N(R1)CONH (R2) is 0 to 70%, and the number of hydroxyl group is 0 to 70%; and the constituent units of polyglutamic acid are bound in any order.

(4) The high molecular weight derivative of a nucleic acid antimetabolite according to (3) above, wherein R is a C1-C4 alkyl group; A is a C2-C4 acyl group; a+b is from 5 to 100 as an average value, wherein a is 80 to 100% of a+b, and b is 0 to 20% of a+b; n is from 50 to 1000 as an average value; and the nucleic acid antimetabolite residue is any one of the nucleic acid antimetabolite residues represented by formula (2):

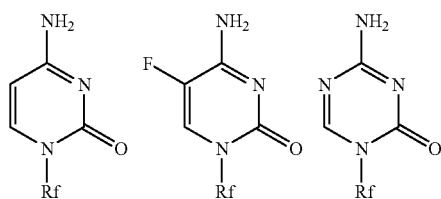

(2)

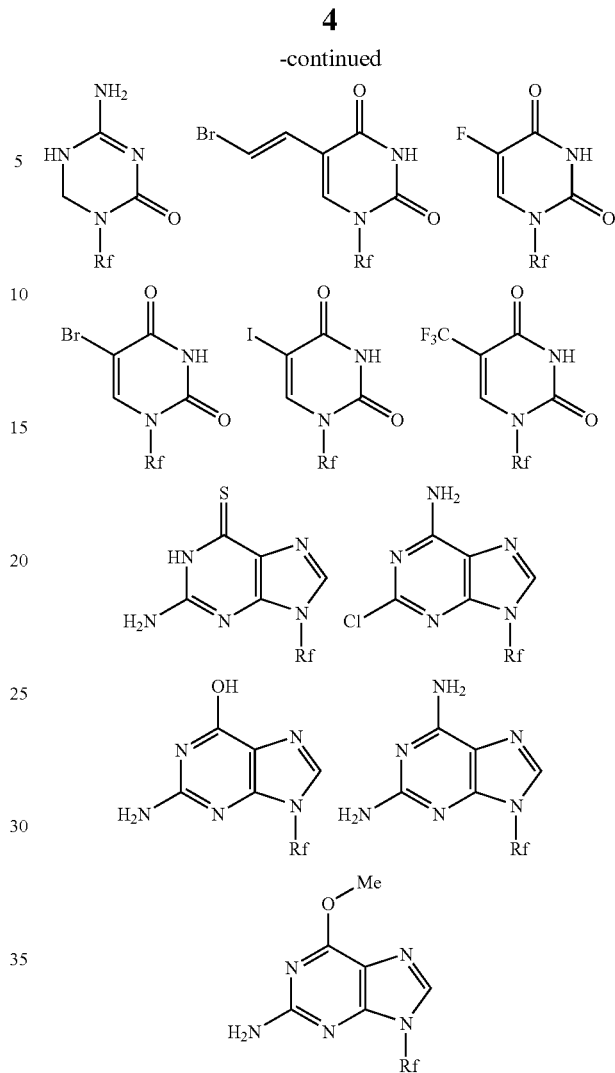

wherein —Rf represents a group selected from the group of substituents of formula (3):

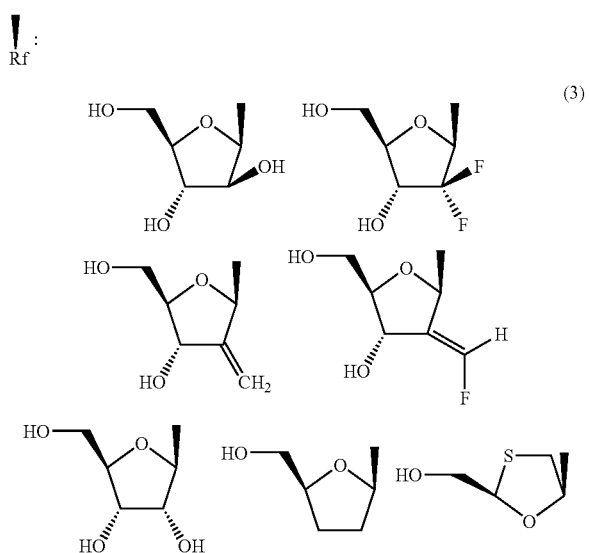

(3)

-continued

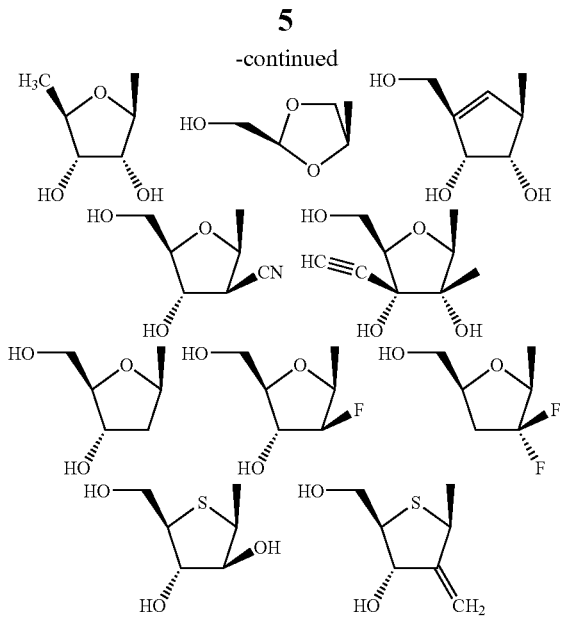

(5) The high molecular weight derivative of a nucleic acid antimetabolite according to (4) above, wherein R is a methyl group; A is an acetyl group; a+b is from 5 to 100 as an average value; n is from 100 to 300 as an average value; and the nucleic acid antimetabolite residue is a residue of gemcitabine or doxifluridine.

(6) The high molecular weight derivative of a nucleic acid antimetabolite according to (1) or (2) above, wherein the high molecular weight derivative of a nucleic acid antimetabolite in which the polymer moiety having a carboxyl group in the side chain is a polyaspartic acid derivative, is a compound represented by the following formula (4):

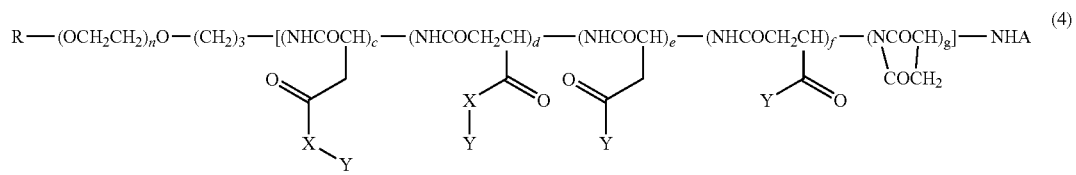

wherein R, A, n and X have the same meanings as defined for formula (1); c+d+e+f+g represents from 3 to 200 as an average value, wherein c+d represents 85 to 100% in c+d+e+f+g, and e+f+g represents 0 to 15% in c+d+e+f+g; Y represents two or more groups selected from the group consisting of a nucleic acid antimetabolite residue, a hydroxyl group, and —N(R1)CONH(R2), wherein R1 and R2 may be identical or different, and are each a C1-C6 alkyl group which may be substituted with a tertiary amino group, wherein, assuming that c+d+e+f+g is 100%, the number of nucleic acid antimetabolite residue is 5 to 80%, the number of —N(R1)CONH(R2) is 0 to 70%, and the number of hydroxyl group is 0 to 70%); and the respective constituent units of polyaspartic acid are bound in any order.

(7) The high molecular weight derivative of a nucleic acid antimetabolite according to (6) above, wherein R is a C1-C4 alkyl group; A is a C2-C4 acyl group; c+d+e+f+g is from 5 to 100 as an average value, wherein c+d is 90 to 100% of c+d+e+f+g, and e+f+g is 0 to 10% of c+d+e+f+g; n is from 50 to 1000 as an average value; and the nucleic acid antimetabolite residue is any one of nucleic acid antimetabolite residues represented by the formula (2).

(8) The high molecular weight derivative of a nucleic acid antimetabolite according to (7) above, wherein R is a methyl group; A is an acetyl group; c+d+e+f+g is from 10 to 60 as an average value; n is from 100 to 300 as an average value; and the nucleic acid antimetabolite residue is a residue of gemcitabine or doxifluridine.

(9) The high molecular weight derivative of a nucleic acid antimetabolite according to anyone of (3) to (8) above, wherein the hydrophobic amino acid residue or hydrophobic amino acid derivative residue is represented by formula (5):

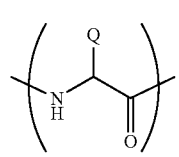

wherein Q represents the side chain of a neutral amino acid.

(10) The high molecular weight derivative of a nucleic acid antimetabolite according to (9) above, wherein Q is an isopropyl group or a benzyl group.

(11) The high molecular weight derivative of a nucleic acid antimetabolite according to (3) above, wherein R is a methyl group; A is an acetyl group; a+b is from 10 to 60 as an average value; n is from 100 to 300 as an average value; the hydrophobic amino acid residue or hydrophobic amino acid derivative residue is a phenylalanine residue; the nucleic acid antimetabolite residue is a gemcitabine residue; and —N(R1)CONH(R2) is an isopropylaminocarbonylisopropylamino group.

(12) The high molecular weight derivative of a nucleic acid antimetabolite according to (6) above, wherein R is a methyl group; A is an acetyl group; c+d+e+f+g is from 10 to 60 as an average value; n is from 100 to 300 as an average value; the hydrophobic amino acid residue or hydrophobic amino acid derivative residue is a phenylalanine residue; the nucleic acid antimetabolite residue is a gemcitabine residue; and —N(R1)CONH(R2) is an isopropylaminocarbonylisopropylamino group.

(13) An antitumor agent comprising the high molecular weight derivative of a nucleic acid antimetabolite according to any one of (1) to (12) above as an active ingredient.

(14) An antiviral agent comprising the high molecular weight derivative of a nucleic acid antimetabolite according to any one of (1) to (12) above as an active ingredient.

(15) A method for manufacturing the high molecular weight derivative of a nucleic acid antimetabolite according to any one of (1) to (12) above, the method comprising introducing the nucleic acid antimetabolite to a carboxyl group in the side chain of a high molecular weight compound comprising a polyethylene glycol moiety and a polymer moiety having a carboxyl group in the side chain via a hydrophobic linker.

(16) The method for manufacturing the high molecular weight derivative of a nucleic acid antimetabolite according to (15) above, the method comprising introducing the nucleic acid antimetabolite to a high molecular weight derivative in which a hydrophobic linker is bound to a carboxyl group of a high molecular weight compound and which is represented by formula (6):

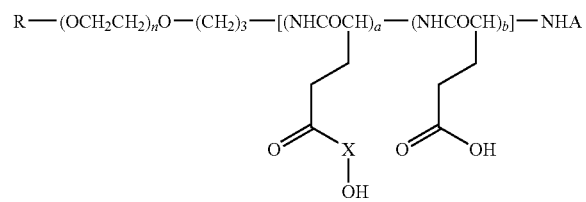

(6)

wherein R, A, n, a, b and X have the same meanings as defined in formula (1).

(17) The method for manufacturing the high molecular weight derivative of a nucleic acid antimetabolite according to (15) above, the method comprising introducing the nucleic acid antimetabolite to a high molecular weight derivative in which a hydrophobic linker is bound to a carboxyl group of a high molecular weight compound and which is represented by formula (7):

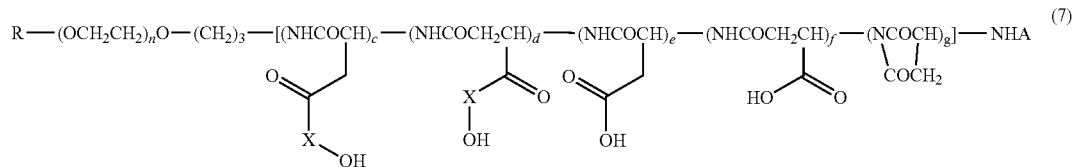

(7)

wherein R, A, n and X have the same meanings as defined in formula (1); and c, d, e, f and g have the same meanings as defined in formula (4).

(18) A high molecular weight derivative represented by the formula (6) described in (16) above, wherein a hydrophobic linker is bound to a carboxyl group in the side chain of the high molecular weight compound.

(19) A high molecular weight derivative represented by the formula (7) described in (17) above, wherein a hydrophobic linker is bound to a carboxyl group in the side chain of the high molecular weight compound.

(20) A high molecular weight derivative having a hydrophobic linker bound to a carboxyl group in the side chain of the high molecular weight compound according to (18) above, wherein R is a methyl group; A is an acetyl group; a+b is from 10 to 60 as an average value; and n is from 100 to 300 as an average value.

(21) A high molecular weight derivative having a hydrophobic linker bound to a carboxyl group in the side chain of the high molecular weight compound according to (19) above, wherein R is a methyl group; A is an acetyl group; c+d+e+f+g is from 10 to 60 as an average value; and n is from 100 to 300 as an average value.

Effects of the Invention

The high molecular weight derivative of a nucleic acid antimetabolite of the present invention is characterized by having a structure in which a carboxyl group in side chain of the high molecular weight compound comprising a polyethylene glycol moiety and a polymer moiety having a carboxyl group in the side chain is linked to a nucleic acid antimetabolite via a hydrophobic linker. This high molecular weight derivative is considered, owing to its structure, to form an aggregate having an outer shell formed of the polyethylene glycol moiety having high affinity with water and an inner shell formed of side chains having a hydrophobic linker, in water. This high molecular weight derivative is capable of slowly releasing a nucleic acid antimetabolite in vivo without depending on enzymes, and is useful as an antitumor agent or antiviral agent having an excellent therapeutic effect at lower doses. Since the high molecular weight derivative exhibits sustained drug release properties without depending on the enzymes in vivo, the high molecular weight derivative can become a derivative of which the therapeutic effect is less affected by the individual differences in patients. Furthermore, the high molecular weight derivative becomes a drug which selectively accumulates at the diseased sites and has superior effects while having fewer adverse effects. The high molecular weight derivative can also has a high content of drug, regardless of the degree of hydrophilicity of the drug. This is attributable to the ability to introduce drugs via a hydrophobic linker.

BEST MODE FOR CARRYING OUT THE INVENTION

The high molecular weight derivative of a nucleic acid antimetabolite of the present invention is characterized in that a nucleic acid antimetabolite is bound to a carboxyl group in the side chain of a high molecular weight compound comprising a polyethylene glycol moiety and a polymer moiety having a carboxyl group in the side chain via a hydrophobic linker.

According to the present invention, the hydrophobic linker may be any substituent that is hydrophobic, and is not particularly limited as long as it does not affect the manifestation of efficacy of the high molecular weight derivative of a nucleic acid antimetabolite. However, preferably, there may be mentioned a hydrophobic amino acid residue or a hydrophobic amino acid derivative.

The "nucleic acid antimetabolite" according to the present invention is a compound having antitumor activity or antiviral activity, and having the structure of a nucleoside derivative. More specifically, the "nucleic acid antimetabolite" is a compound in which the nucleic acid base moiety is any one selected from the aforementioned formula (2), and the group bound thereto (Rf) is any one selected from the aforementioned formula (3).

Even more specifically, the examples include, but are not limited to, for example, cytarabine, gemcitabine, doxifluridine, azacitidine, decitabine, nelarabine, 2'-methylidene-2'-deoxycytidine (DMDC), tezacitabine, zalcitabine, lamivudine, 5'-deoxy-5-fluorocytidine (5'-DFCR), troxacitabine, 3'-ethynylcytidine, 2'-cyano-2'-deoxy-1-β-D-arabinofuranocylcytosine (CNDAC) and the like.

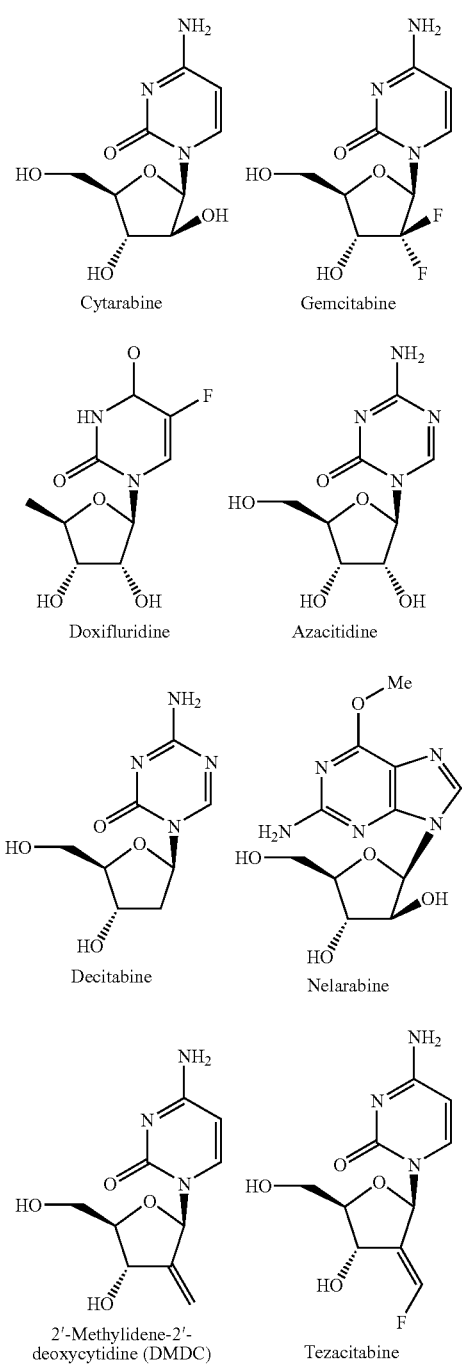

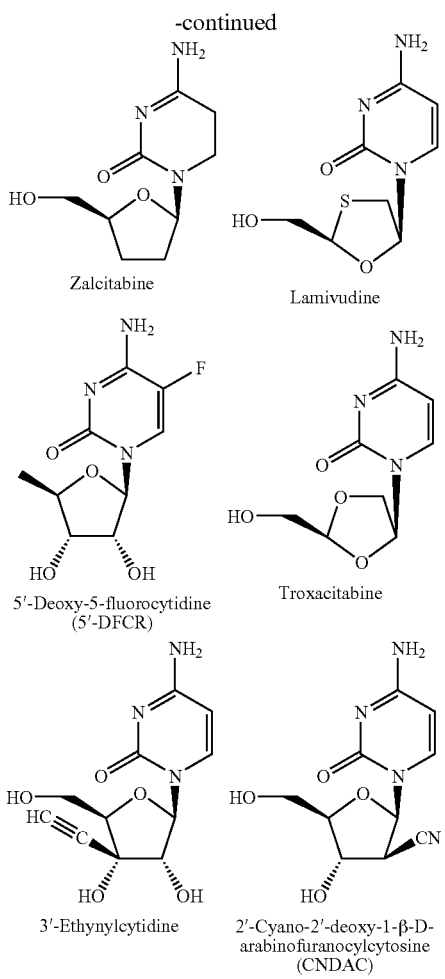

As for the polymer moiety having a carboxyl group in the side chain in the "high molecular weight compound comprising a polyethylene glycol moiety and a polymer moiety having a carboxyl group in the side chain" according to the present invention, there may be mentioned a graft type polymer in which the side chain having a carboxyl group is branched out from the polymer backbone, a block type polymer resulting from condensation of a polycarboxylic acid polymer, or the like.

As for the aforementioned high molecular weight compound in which the polymer moiety having a carboxyl group in the side chain is a graft type polymer, there may be mentioned, for example, the polymer described in JP-A No. 11-279083, which is obtained by subjecting polyethylene glycol, a condensate of an acrylic acid, and an acrylic acid or maleic anhydride to a copolymerization reaction, and if necessary, subjecting the product to a hydrolysis reaction, or the like.

As for the aforementioned high molecular weight compound in which the polymer moiety having a carboxyl group in the side chain is a block type polymer, there may be mentioned a compound in which a polyethylene glycol having terminal functional groups is linked to a polycarboxylic acid having terminal functional groups, or the compounds described in Patent Documents 3, 4 and 5, which are obtained by a polymerization reaction in which activated amino acids capable of initiating polymerization are linked to a polyethylene glycol having amino groups at the ends of the chain.

Examples of the polymer having a carboxyl group in the side chain include polyacrylic acid, polymethacrylic acid, polymalic acid, polyaspartic acid, polyglutamic acid, and the like, and preferred is polyaspartic acid or polyglutamic acid.

The "polyethylene glycol" according to the present invention may also be a polyethylene glycol derivative modified at both ends of chain or at a single end of chain, and in that case, the modifying groups at the both ends of the chain may be identical or different. As the modifying group at the end of the chain, a C1-C6 alkyl group which may be substituted may be mentioned, and a C1-C4 alkyl group which may be substituted is preferred.

According to the present invention, the C1-C6 alkyl group of the C1-C6 alkyl group which may be substituted may include a straight-chained, branched or cyclic C1-C6 alkyl group, and examples thereof include a methyl group, an ethyl group, a propyl group, an isopropyl group, a butyl group, an isobutyl group, a tert-butyl group, a pentyl group, an isopentyl group, a 2-methylbutyl group, a neopentyl group, a 1-ethylpropyl group, a hexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, a 2-ethylbutyl group, a cyclopropyl group, a cyclopentyl group, a cyclohexyl group, and the like. A C1-C4 alkyl group is preferred, and examples thereof include a methyl group, an ethyl group, an n-propyl group, an isopropyl group, an n-butyl group, an s-butyl group, a t-butyl group, and the like, and particularly preferred is a methyl group, an ethyl group, an n-propyl group or an isopropyl group.

According to the present invention, the substituents for the C1-C6 alkyl group which may be substituted include, but are not particularly limited to, for example, an amino group, a methylamino group, a dimethylamino group, an ethylamino group, a diethylamino group, and the like may be mentioned, and an amino group is preferred.

According to the present invention, a polyethylene glycol derivative modified at both ends of the chain is preferred, and specifically, a polyethylene glycol derivative having a C1-C6 alkyl group at one end and an amino-C1-C6 alkyl group at the other end may be mentioned. A polyethylene glycol derivative having a C1-C4 alkyl group at one end and an amino-C1-C4 alkyl group at the other end is preferred, and particularly, a polyethylene glycol derivative having a methyl group at one end and an aminopropyl group at the other end is preferred.

The weight average molecular weight of the "polyethylene glycol" according to the present invention is about 200 to 500,000, preferably about 500 to 100,000, and more preferably about 2,000 to 50,000.

The "high molecular weight compound comprising a polyethylene glycol moiety and a polymer moiety having a carboxyl group in the side chain" according to the present invention is preferably a block type polymer, and more preferably a block copolymer of a polyethylene glycol and a polymer having a carboxyl group in the side chain.

The block copolymer of a polyethylene glycol and a polymer having a carboxyl group in the side chain according to the present invention may includes, for example, alkoxypolyethylene glycol-polyacrylic acid, alkoxypolyethylene glycol-polymethacrylic acid, methoxypolyethylene glycol-polyaspartic acid, alkoxypolyethylene glycol-polyglutamic acid, and the like, while preferred is methoxypolyethylene glycol-polyaspartic acid or methoxypolyethylene glycol-polyglutamic acid.

The average number of carboxyl groups per molecule of the "high molecular weight compound comprising a polyethylene glycol moiety and a polymer moiety having a carboxyl group in the side chain" according to the present invention is about 3 to 200, preferably about 5 to 100, and more preferably about 10 to 60.

The weight average molecular weight of the "high molecular weight compound comprising a polyethylene glycol moiety and a polymer moiety having a carboxyl group in the side chain" according to the present invention is about 500 to 500,000, preferably about 2,000 to 100,000, and more preferably about 3,000 to 50,000.

According to the present invention, the amount of the nucleic acid antimetabolite linked via a hydrophobic linker to a carboxyl group in the side chain of the high molecular weight compound comprising a polyethylene glycol moiety and a polymer moiety having a carboxyl group in the side chain, is not particularly limited as long as the amount is in the range of 1 to the total number of carboxyl groups, and is preferably an amount exhibiting efficacy when administered in vivo. Preferably, the amount is 5 to 80%, and more preferably 5 to 70%, of the total number of carboxylic acids in the polymer moiety.

The aforementioned linking amount can be determined from the intensity of the ultraviolet absorption spectrum of the compound of the present invention. Furthermore, the amount of binding can also be determined by quantifying the nucleic acid antimetabolite which is liberated by alkali-hydrolyzing the high molecular weight derivative of a nucleic acid antimetabolite of the present invention, for example, by high performance liquid chromatography or the like.

The high molecular weight derivative of a nucleic acid antimetabolite of the present invention is characterized in that a nucleoside derivative which is a nucleic acid antimetabolite is linked to a carboxyl group in the side chain of a high molecular weight compound comprising a polyethylene glycol moiety and a polymer moiety having a carboxyl group in the side chain via a hydrophobic linker, and preferably the polymer moiety having a carboxyl group in the side chain is a derivative of polyaspartic acid or polyglutamic acid. Even more preferably, the high molecular weight derivative is a compound represented by the above-described formula (1), wherein R represents a hydrogen atom or a C1-C6 alkyl group; A represents a hydrogen atom, a C1-C6 acyl group or a C1-C6 alkoxycarbonyl group; a+b represents 3 to 200 as an average value, wherein a represents 75 to 100% of a+b, and b represents 0 to 25% of a+b; n represents 5 to 2000 as an average value; X represents a hydrophobic amino acid residue or a hydrophobic amino acid derivative residue; Y represents two or more groups selected from the group consisting of a nucleic acid antimetabolite residue, a hydroxyl group, and —N(R1)CONH(R2), wherein R1 and R2 may be identical or different, and are each a C1-C6 alkyl group which may be substituted with a tertiary amino group, wherein, assuming that a+b is 100%, the number of nucleic acid antimetabolite residue is 5 to 80%, the number of —N(R1)CONH(R2) is 0 to 70%, and the number of hydroxyl group is 0 to 70%); and the order of binding of the constituent units of polyglutamic acid is arbitrary, and by the above-described formula (4), wherein R, A, n and X have the same meanings as defined in formula (1); c+d+e+f+g represents 3 to 200 as an average value, wherein c+d represents 85 to 100% of c+d+e+f+g, and e+f+g represents 0 to 15% of c+d+e+f+g; Y represents two or more groups selected from the group consisting of a nucleic acid antimetabolite residue, a hydroxyl group, and —N(R1)CONH(R2), wherein R1 and R2 may be identical or different, and are each a C1-C6 alkyl group which may be substituted with a tertiary amino group, wherein, assuming that c+d+e+f+g is 100%, the number of nucleic acid antimetabolite is 5 to 80%, the number of —N(R1)CONH(R2) is 0 to 70%, and the number of hydroxyl group is 0 to 70%); and the order of biding of the respective constituent units of polyaspartic acid is arbitrary.

Furthermore, the high molecular weight derivative having a hydrophobic linker bound to a carboxyl group in the side chain of the high molecular weight compound of the present invention is a compound represented by the above-described formula (6), wherein R, A, n, a, b and X have the same meanings as defined in formula (1), and the above-described formula (7), wherein R, A, n and X have the same meanings as defined in formula (1); and c, d, e, f and g have the same meanings as defined in formula (4). By introducing a nucleoside derivative which is a nucleic acid antimetabolite, to the high molecular weight derivative having a hydrophobic linker bound to a carboxyl group in the side chain of the high molecular weight compound of the present invention, the high molecular weight derivative of a nucleic acid antimetabolite of the present invention can be obtained.

In the formula (1), formula (4), formula (6) and formula (7), the C1-C6 alkyl group for R has the same meaning as the above-mentioned alkyl group, and preferred groups are also similar.

In the formula (1), formula (4), formula (6) and formula (7), the C1-C6 acyl group for A may be exemplified by, for example, a formyl group, an acetyl group, a propionyl group, a butyryl group, an isobutyryl group, a valeryl group, an isovaleryl group, a pivaloyl group or a hexanoyl group, and preferred is a C2-C4 acyl group, for example, an acetyl group or a propionyl group, and an acetyl group is more preferred.

In the formula (1), formula (4), formula (6) and formula (7), the C1-C6 alkoxycarbonyl group for A may be exemplified by, for example, a methoxycarbonyl group, an ethoxycarbonyl group, a propoxycarbonyl group, an isopropoxycarbonyl group, an n-butoxycarbonyl group, a tert-butoxycarbonyl group, a pentoxycarbonyl group, a hexyloxycarbonyl group, a cyclopropoxycarbonyl group, a cyclopentyloxycarbonyl group or a cyclohexyloxycarbonyl group, and preferred are a methoxycarbonyl group, an ethoxycarbonyl group, a propoxycarbonyl group, an isopropoxycarbonyl group, a butoxycarbonyl group and a tert-butoxycarbonyl group, and an ethoxycarbonyl group or a tert-butoxycarbonyl group is more preferred.

In the formula (1), formula (4), formula (6) and formula (7), n is from 5 to 2000 as an average value, preferably about 50 to 1000, and more preferably about 100 to 300.

In the formula (1) and formula (6), a+b is from 3 to 200 as an average value, preferably about 5 to 100, and more preferably about 10 to 60.

In the formula (1) and formula (6), a is 75 to 100%, and preferably 80 to 100%, of a+b, and b is 0 to 25%, and preferably 0 to 20%, of a+b.

In the formula (4) and formula (7), c+d+e+f+g is from 3 to 200 as an average value, preferably about 5 to 100, and more preferably about 10 to 60.

In the formula (4) and formula (7), c+d is 85 to 100%, and preferably 90 to 100%, of c+d+e+f+g, and e+f+g is 0 to 15%, and preferably 0 to 10%, of c+d+e+f+g.

In the formula (1) and formula (6), the parenthesized constituent units of a or b may be linked randomly, or may also be linked so as to form blocks. Y may also be such that the nucleic acid antimetabolite, the hydroxyl group and —N(R1)CONH(R2) are linked randomly, or linked so as to form blocks (provided that, assuming a+b to be 100%, the number of nucleic acid antimetabolite residue is 5 to 80%, the number of —N(R1)CONH(R2) is 0 to 70%, and the number of hydroxyl group is 0 to 70%). In the formula (1), a particularly preferred nucleic acid antimetabolite for Y may be exemplified by gemcitabine.

In the formula (4) and formula (7), the parenthesized constituent units of c, d, e, f and g may be linked randomly, or may also be linked so as to form blocks. Y may also be such that the nucleic acid antimetabolite, the hydroxyl group and —N(R1)CONH(R2) are linked randomly, or linked so as to form blocks (provided that, assuming c+d+e+f+g to be 100%, the number of nucleic acid antimetabolite residue is 5 to 80%, the number of —N(R1)CONH(R2) is 0 to 70%, and the number of hydroxyl group is 0 to 70%). In the formula (4), a particularly preferred nucleic acid antimetabolite for Y may be exemplified by gemcitabine.

In the formula (1), formula (4), formula (6) and formula (7), the hydrophobic linker for X may be exemplified by various substituents. The hydrophobic linker is not particularly limited as long as it does not affect the manifestation of efficacy of the high molecular weight derivative of a nucleic acid antimetabolite, but may be preferably exemplified by a hydrophobic amino acid residue or a hydrophobic amino acid derivative residue, and more preferably a group represented by an α-amino acid or α-amino acid derivative represented by the above-described formula (5), wherein Q represents the side chain of a neutral amino acid.

The side chain of neutral amino acid for Q in the formula (5) may include, for example, side chains for natural amino acid residues, such as a hydrogen atom, a methyl group, an isopropyl group, an isobutyl group, an s-butyl group, a benzyl group, a hydroxymethyl group, a 1-hydroxyethyl group, a carbamoylmethyl group and 2-carbamoylethyl group; side chains for amino acid residue derivatives, such as a tert-butoxymethyl group, a benzyloxymethyl group, a benzyloxycarbonylmethyl group, and a 2-benzyloxycarbonylethyl group; and the like. An isopropyl group, an isobutyl group, an s-butyl group, a benzyl group, a benzyloxymethyl group, a benzyloxycarbonylmethyl group, a 2-benzyloxycarbonylethyl group and the like are preferred, and an isopropyl group, a benzyl group, a benzyloxymethyl group and a 2-benzyloxycarbonylethyl group are more preferred, and a benzyl group is particularly preferred.

In the formula (1) and formula (4), —N(R1)CONH(R2) for Y is not particularly limited as long as it does not affect the manifestation of efficacy of the high molecular weight derivative of a nucleic acid antimetabolite, but preferably, there may be mentioned a group in which R1 and R2 of —N(R1)CONH (R2) may be identical or different, and are each represented by a C1-C6 alkyl group which may be substituted by a tertiary amino group. More preferably, the group is a cyclohexylaminocarbonylcyclohexylamino group, or an isopropylaminocarbonylisopropylamino group.

Here, the C1-C6 alkyl group of the C1-C6 alkyl group which may be substituted with a tertiary amino group for R1 and R2 in —N(R1)CONH(R2), has the same meaning as the above-mentioned alkyl group, and preferred groups are also similar.

In the formula (1) and formula (4), for the total number of carboxyl groups of the polymer, the proportion of Y being a nucleic acid antimetabolite residue is 5 to 80%, and preferably 5 to 70%; the proportion of Y being a hydroxyl group is 0 to 70%, and preferably 5 to 60%; and the proportion of Y being —N(R1)CONH(R2) is 0 to 70%, and preferably 0 to 60%.

In the high molecular weight derivative of a nucleic acid antimetabolite of the present invention, when there are side chain carboxyl groups not bound by a nucleic acid antimetabolite or the like, these carboxyl groups may be in a free form, or in the form of a salt of an alkali. In the case where the carboxyl group has been obtained in a free form, the carboxyl group can be converted to a desired salt according to a known method or a method equivalent thereto. On the other hand, in the case where the carboxyl group has been obtained as a salt, the salt can be converted to a free form or another desired salt according to a known method or a method equivalent thereto.

Examples of the salt of an alkali include lithium salts, sodium salts, potassium salts, magnesium salts, ammonium salts, triethylammonium salts, and the like.

The structural unit constituting the polymer moiety having a carboxyl group in the side chain in the high molecular constituent units is not particularly limited, and may be of block type as well as random type. The proportion of the α-amino acid type (c+e) with respect to the total number of aspartic acids (c+d+e+f+g) is 10 to 100%, and preferably 20 to 100%. This proportion can be appropriately changed by, for example, selecting the deprotection conditions for the protective group of polyaspartic acid, or the like.

As for the particularly preferred compounds as the high molecular weight derivative of a nucleic acid antimetabolite of the present invention, for example, the compounds shown in the following Table 1 may be mentioned.

In the Table 1, Phe represents phenylalanine. As for the nucleic acid antimetabolite residue of Y, there may be mentioned the respective residues of cytarabine, gemcitabine, doxifluridine, azacitidine, decitabine, nelarabine, tezacitabine, 5'-deoxy-5-fluorocytidine, 2'-deoxy-2'-methylidenecytidine (DMDC), 3'-ethynylcytidine, 2'-C-cyano-2'-deoxy-1-beta-D-arabinofuranocylcytosine (CNDAC), troxacitabine, and (−)-beta-L-dioxolanecytidine.

TABLE 1

| Compound No. | Formula | R | n (average) | a + b (average) | c + d + e + f + g (average) | A | X: hydrophobic linker | Nucleic acid antimetabolite |
|---|---|---|---|---|---|---|---|---|
| 1 | (1) | CH₃ | 272 | 10-40 | | CH₃CO | Phe | Gemcitabine |
| 2 | (1) | CH₃ | 272 | 10-40 | | CH₃CO | Phe | Doxifluridine |
| 3 | (1) | CH₃ | 272 | 10-40 | | CH₃CO | Phe | Cytarabine |
| 4 | (1) | CH₃ | 272 | 10-40 | | CH₃CO | Phe | Azacitidine |
| 5 | (1) | CH₃ | 272 | 10-40 | | CH₃CO | Phe | Decitabine |
| 6 | (1) | CH₃ | 272 | 10-40 | | CH₃CO | Phe | Nelarabine |
| 7 | (1) | CH₃ | 272 | 10-40 | | CH₃CO | Phe | Tezacitabine |
| 8 | (1) | CH₃ | 272 | 10-40 | | CH₃CO | Phe | 5'-Deoxy-5-fluorocytidine |
| 9 | (1) | CH₃ | 272 | 10-40 | | CH₃CO | Phe | 2'-Deoxy-2'-methylidenecytidine |
| 10 | (1) | CH₃ | 272 | 10-40 | | CH₃CO | Phe | 3'-Ethynylcytidine |
| 11 | (1) | CH₃ | 272 | 10-40 | | CH₃CO | Phe | 2'-C-cyano-2'-deoxy-1-beta-D-arabinofuranocylcytosine |
| 12 | (1) | CH₃ | 272 | 10-40 | | CH₃CO | Phe | Troxacitabine |
| 13 | (1) | CH₃ | 272 | 10-40 | | CH₃CO | Phe | (—)-beta-L-dioxolanecytidine |
| 14 | (4) | CH₃ | 272 | | 10-45 | CH₃CO | Phe | Gemcitabine |
| 15 | (4) | CH₃ | 272 | | 10-45 | CH₃CO | Phe | Doxifluridine |
| 16 | (4) | CH₃ | 272 | | 10-45 | CH₃CO | Phe | Cytarabine |
| 17 | (4) | CH₃ | 272 | | 10-45 | CH₃CO | Phe | Azacitidine |
| 18 | (4) | CH₃ | 272 | | 10-45 | CH₃CO | Phe | Decitabine |
| 19 | (4) | CH₃ | 272 | | 10-45 | CH₃CO | Phe | Nelarabine |
| 20 | (4) | CH₃ | 272 | | 10-45 | CH₃CO | Phe | Tezacitabine |
| 21 | (4) | CH₃ | 272 | | 10-45 | CH₃CO | Phe | 5'-Deoxy-5-fluorocytidine |
| 22 | (4) | CH₃ | 272 | | 10-45 | CH₃CO | Phe | 2'-Deoxy-2'-methylidenecytidine |
| 23 | (4) | CH₃ | 272 | | 10-45 | CH₃CO | Phe | 3'-Ethynylcytidine |
| 24 | (4) | CH₃ | 272 | | 10-45 | CH₃CO | Phe | 2'-C-cyano-2'-deoxy-1-beta-D-arabinofuranocylcytosine |
| 25 | (4) | CH₃ | 272 | | 10-45 | CH₃CO | Phe | Troxacitabine |
| 26 | (4) | CH₃ | 272 | | 10-45 | CH₃CO | Phe | (—)-beta-L-dioxolanecytidine | weight derivative of a nucleic acid antimetabolite of the present invention, may be an optically active form in the case where optical isomers exist, or a racemic form, or a mixture at an arbitrary ratio. For example, if the polymer moiety having a carboxyl group in the side chain is a polyglutamic acid derivative, a polymer in which poly-L-glutamic acid, poly-D-glutamic acid, L-glutamic acid having a substituted side chain, and D-glutamic acid having a substituted side chain are linked at any proportions in any order of binding, is acceptable.

Furthermore, in the case where the polymer moiety having a carboxyl group in the side chain is a polyaspartic acid derivative, there are the aforementioned optical isomers, as well as the α-amino acid type structural units of units c and e in the formulas (4) and (7), which are indicated with parentheses, the β-amino acid type structural units of units d and f, and the cyclized type structural unit of unit g. The order of binding for these α- and β-amino acid type or cyclized type The high molecular weight derivative of a nucleic acid antimetabolite of the present invention can be manufactured, for example, by condensing a methoxypolyethylene glycol-polyaspartic acid block copolymer or a methoxypolyethylene glycol-polyglutamic acid block copolymer that has been produced according to the methods described in Patent Documents, 3, 4 and 5, with an amino acid derivative having a protected carboxyl group using a dehydrating condensing agent in a solvent, and then condensing a new carboxyl group of a high molecular weight derivative of formula (6) or formula (7) having a carboxyl group newly produced after deprotection, with a nucleic acid antimetabolite using a dehydrating condensing agent in a solvent, but the manufacturing method is not limited to this particular method.

Here, with regard to the high molecular weight derivative of a nucleic acid antimetabolite of the present invention, there are a case where the nucleic acid antimetabolite is bound to a carboxyl group of the high molecular weight derivative represented by formula (6) or formula (7) via an ester linkage; a case where the nucleic acid antimetabolite is bound to a carboxyl group of the high molecular weight derivative represented by formula (6) or formula (7) via an ester linkage and an amide linkage; and a case where the nucleic acid antimetabolite is bound to a carboxyl group of the high molecular weight derivative represented by formula (6) or formula (7) via an amide linkage. In this regard, the mode of binding by which the antimetabolite is introduced is determined depending on the dehydrating condensing agent used, but any mode of binding may be used in the present invention.

With regard to the aforementioned manufacturing method, the solvent for the dehydration condensation reaction (amidation) of the amino acid and amino acid derivative having a protected carboxyl group, which serves as the linker, is not particularly limited as long as the reaction proceeds, but there may be mentioned, for example, aromatic hydrocarbons such as toluene and xylene; halogenated hydrocarbons such as methylene chloride, chloroform and 1,2-dichloroethane; ethers such as tetrahydrofuran, dioxane, dimethoxyethane, and diethylene glycol dimethyl ether; nitriles such as acetonitrile and propionitrile; amides such as dimethylformamide, dimethylacetamide, and N-methylpyrrolidone; ureas such as 1,3-dimethylimidazolidinone; or solvent mixtures of the above-mentioned solvents. Amides and ureas are preferred, and dimethylformamide or 1,3-dimethylimidazolidinone is more preferred.

The dehydrating condensing agent is not particularly limited as long as the condensation reaction between an amine and a carboxyl group proceeds, but preferably, the dehydrating condensing agent is dicyclohexylcarbodiimide, diisopropylcarbodiimide, 1-dimethylaminopropyl-3-ethylcarbodiimide, carbonyldiimidazole, isobutyl chloroformate, pivalic acid chloride, DMT-MM (4-(4,6-dimethoxy-1,3,5-triazin-2-yl)-4-methylmorpholinium chloride), TFFH (tetramethylfluoroformamidinium hexafluorophosphate), 1-ethoxycarbonyl-2-ethoxy-1,2-dihydroxyquinolinone (EEDQ), or BOP (benzotriazol-1-yloxytris(dimethylamino)phosphonium hexafluorophosphate).

During the dehydration condensation reaction, a reaction aid may also be used, and examples of the reaction aid include N-hydroxysuccinimide, 1-hydroxybenzotriazole, 4-dimethylaminopyridine, 2,6-di-t-butyl-4-methylpyrridine, and the like.

The reaction temperature of the dehydration condensation reaction is usually from 4 to 60° C., and preferably from room temperature to 50° C. The reaction time is from 2 hours to several days, and preferably from 4 to 48 hours.

In the above-described production method, the method of removing the protective group, which is carried out after the introduction of the amino acid and amino acid derivative having a protected carbonyl group, may be carried out using appropriate methods for the respective protective groups used, and are carried out according to known methods. For example, a benzyl group can be removed by hydrogenolysis by means of catalytic reduction. By removing the protective group, the high molecular weight derivatives of the present invention represented by formula (6) and (7) can be obtained.

In regard to the aforementioned manufacturing method, the solvent for the dehydration condensation reaction for introducing the nucleic acid antimetabolite to a carbonyl group which is newly generated by deprotection, is not particularly limited as long as the reaction proceeds, but the same solvents as the solvents that can be used upon performing the dehydration condensation of the methoxypolyethylene glycol-polyaspartic acid block copolymer or methoxypolyethylene glycol-polyglutamic acid block copolymer with the amino acid derivative, can be used. Preferred solvents are also similar.

The dehydrating condensing agent is not particularly limited as long as the condensation reaction between the nucleic acid metabolite and the carboxyl group proceed, but the same dehydrating condensing agents as the dehydrating condensing agents that can be used upon condensing by dehydration the aforementioned methoxypolyethylene glycol-polyaspartic acid block copolymer or methoxypolyethylene glycol-polyglutamic acid block copolymer with the amino acid derivative, can be used. Preferred dehydrating condensing agents are also similar. Particularly preferred may be carbodiimide-based condensing agents such as dicyclohexylcarbodiimide, diisopropylcarbodiimide and 1-dimethylaminopropyl-3-ethylcarbodiimide, 2-ethoxy-1-ethoxycarbonyl-1,2-dihydroquinoline (EEDQ), and the like.

During the dehydration condensation reaction, a reaction aid may also be used, and examples of the reaction aid include N-hydroxysuccinimide, 1-hydroxybenzotriazole, 4-dimethylaminopyridine, 2,6-di-t-butyl-4-methylpyridine, and the like.

The reaction temperature of the dehydration condensation reaction is usually from 4 to 60° C., and preferably from 15 to 50° C. The reaction time is from one hour to several days, and preferably from 4 to 48 hours.

After the aforementioned reaction, the target compound can be isolated and purified, if necessary, by appropriately applying separation techniques that are known per se, for example, concentration under reduced pressure, solvent extraction, crystallization, dialysis, chromatography and the like.

The above-described dehydration condensation reaction gives a high molecular weight derivative of a nucleic acid antimetabolite of the present invention in which Y is two or more groups selected from the group consisting of a nucleic acid antimetabolite residue, a hydroxyl group and —N(R1) CONH(R2), wherein R1 and R2 may be identical or different, and are each a C1-C6 alkyl group which may be substituted with a tertiary amino group. Furthermore, in the group that is introduced to Y, or in the high molecular weight derivative of a nucleic acid antimetabolite, the mode of binding between the high molecular weight derivative of formula (6) or formula (7) and the nucleic acid antimetabolite can be changed as follows by means of the dehydrating condensing agent used or the like.

For example, when a carbodiimide-based dehydrating condensing agent is used as the dehydrating condensing agent, a high molecular weight derivative of a nucleic acid antimetabolite of the present invention in which Y is two or more groups selected from the group consisting of a nucleic acid antimetabolite residue, a hydroxyl group and —N(R1)CONH (R2), wherein R1 and R2 may be identical or different and are each a C1-C6 alkyl group which may be substituted with a tertiary amino group, is obtained. In the high molecular weight derivative of a nucleic acid antimetabolite, the mode of binding between the high molecular weight derivative of formula (6) or formula (7) and the nucleic acid antimetabolite, is thought to be mainly an ester linkage formed by a reaction with a hydroxyl group of the nucleic acid antimetabolite under the influence of the reactivity of a functional group, such as a hydroxyl group or an amino group, of the nucleic acid antimetabolite. In this case, there may be cases where a plurality of the modes of binding with the nucleic acid antimetabolite can exist depending on the functional group possessed by the nucleic acid antimetabolite, but as long as the mode of binding does not affect the manifestation of efficacy of the high molecular weight derivative of a nucleic acid antimetabolite, the mode of binding may be mixed or may be the same.

Furthermore, for example, when EEDQ is used as the dehydrating condensing agent, a high molecular weight derivative of a nucleic acid antimetabolite of the present invention in which Y is a nucleic acid antimetabolite residue and a hydroxyl group, is obtained. The mode of binding between the high molecular weight derivative of formula (6) or formula (7) and the nucleic acid antimetabolite in the aforementioned high molecular weight derivative of a nucleic acid antimetabolite, is thought to be mainly an amide linkage formed by an amino group of a cytidine-based antimetabolite of the nucleic acid antimetabolite, based on the reaction mechanism of EEDQ.

When introducing only the group —N(R1)CONH(R2), wherein R1 and R2 may be identical or different and are each a C1-C6 alkyl group which may be substituted with a tertiary amino group, as Y to the high molecular weight derivative of formula (6) or formula (7), the group can be introduced by using the above-mentioned carbodiimide-based dehydrating condensing agent, without a nucleic acid antimetabolite.

Here, a compound having a linker bound to a nucleic acid antimetabolite may be separately synthesized and introduced to the high molecular weight compound comprising a polyethylene glycol moiety and a polymer moiety having a carboxyl group in the side chain, but in order to avoid the reaction and decomposition of the nucleic acid antimetabolite which is an active body having a polyfunctional group, it is preferable to link the nucleic acid antimetabolite at the final process.

The high molecular weight derivative of a nucleic acid antimetabolite of the present invention may form, in an aqueous solution, a micelle having the polyethylene glycol moiety as an outer shell. The formation of micelles can be verified by a gel permeation chromatography (GPC) method, a dynamic light scattering method, or the like.

According to the invention, it is possible, by freely changing the hydrophobicity of the linker, to introduce various hydrophilic drugs to the high molecular weight derivative of formula (6) or formula (7) at a high content, without losing the property of forming aggregates.

The present invention also includes an antitumor agent or antiviral agent, which comprises the high molecular weight derivative of a nucleic acid antimetabolite described above as an active ingredient. The high molecular weight derivative of a nucleic acid antimetabolite can be administered directly, or can also be administered as a pharmaceutical composition in which the high molecular weight derivative is mixed with pharmaceutically acceptable materials. The dosage form of the pharmaceutical composition may be any one of injections, a powder preparation, granules, tablets, suppository, and the like. These preparations may also contain various auxiliary agents that are used for pharmaceutical purposes, namely, carriers or other aids, for example, additives such as stabilizers, preservatives, soothing agents and emulsifiers.

The content of the high molecular weight derivative of a nucleic acid antimetabolite in the preparation may vary with the preparation, but the content is usually 0.1 to 100% by weight, and preferably 1 to 98% by weight.

The application of the antitumor agent of the present invention, which comprises the high molecular weight derivative of a nucleic acid antimetabolite as an active ingredient, is not particularly limited, but the antitumor agent can be used for, for example, non-small cell lung cancer, pancreatic cancer, gastric cancer, colon cancer, rectal cancer, breast cancer, ovarian cancer, bladder cancer, AIDS-associated Kaposi's sarcoma, and the like.

The application of the antiviral agent of the present invention, which comprises the high molecular weight derivative of a nucleic acid antimetabolite as an active ingredient, is not particularly limited, but for example, the antiviral agent can be used for acquired immunodeficiency syndrome (AIDS), herpes zoster, herpes simplex virus infection, and the like, and can also be used for the purpose of preventing infection.

As for the method of administering the high molecular weight derivative of a nucleic acid antimetabolite of the present invention, any method of administration such as oral, injection, rectal administration, intraportal administration, mixing with the perfusate of an organ, or topical administration to the organ of diseased site, can be used. However, parenteral administration is preferred, while more preferred is intravenous administration by injection, intraarterial administration, or topical administration to the organ of diseased site. The dosage of the high molecular weight derivative of a nucleic acid antimetabolite of the present invention varies with the disease condition, method of administration, condition, age and weight of the patient, and the like, but the dosage is usually 1 mg to 5000 mg, and preferably 10 mg to 2000 mg, in terms of the nucleic acid antimetabolite, per $m^2$ of the body surface area, and this may be administered once a day or in several divided portions a day. Furthermore, while this administration can be carried out for several consecutive days, the administration can also be repeated at an interval of several days or several months. If necessary, methods of administration, dosage and administration schedule other than those described above can also be used.

The case where the high molecular weight derivative of the present invention acts as a prodrug, is also included in the present invention. Here, the prodrug is a chemical derivative of a biologically active parent compound, which liberates the parent compound in vivo when administered.

EXAMPLES

Hereinafter, the present invention will be described in more detail by presenting Examples, Reference Examples and Test Examples, but the scope of the present invention is not intended to be limited to these examples.

Reference Example 1

Synthesis of N-acetylation Product of Block Copolymer of Monomethoxypolyethylene Glycol Having Molecular Weight of about 12000 and Polyglutamic Acid Having a Polymerization Number of about 26

A polyethylene glycol having a methoxy group at one end and a 3-aminopropyl group at the other end (SUNBRIGHT META-12T, manufactured by Nippon Fat & Oil Co., Ltd., average molecular weight 12000, 9.60 g) was dissolved in dimethylsulfoxide (200 mL), and γ-benzyl-L-glutamate N-carboxylic acid anhydride (BLG-NCA, 6.15 g; 30 equivalents relative to the polyethylene glycol) was added thereto. The mixture was stirred overnight at 30° C. The reaction liquid was added dropwise to a mixed solvent of isopropyl ether-ethanol (4:1, 3.0 L) under stirring, and the resulting mixture was stirred for another one hour. A precipitate separated out there from was collected by filtration, and was washed with a mixed solvent of isopropyl ether-ethanol (4:1, 500 mL). The obtained product (14.25 g) was dissolved in N,N-dimethylformamide (220 mL), acetic anhydride (4.28 mL) was added thereto, and the mixture was stirred overnight at 30° C. The mixture was added dropwise to a mixed solvent of isopropyl ether-ethyl acetate (4:1, 2.2 L) under stirring, and the resulting mixture was stirred for another one hour. A precipitate separated out therefrom was collected by filtration, and was washed with a mixed solvent of isopropyl ether-ethyl acetate (4:1, 400 mL). The obtained product (12.0 g out of 13.5 g) was dissolved in N,N-dimethylformamide (195 mL), 5% palladium-carbon (water content 55%, 1.20 g) was added thereto, and the mixture was stirred overnight at room temperature in a hydrogen atmosphere. The palladium-carbon was separated by filtration, and then the filtrate was added dropwise to a mixed solvent of isopropyl ether-ethyl acetate (4:1, 2.0 L) under stirring. The resulting mixture was stirred for another one hour. A precipitate separated out therefrom was collected by filtration, and was washed with a mixed solvent of isopropyl ether-ethyl acetate (4:1, 300 mL). The obtained product was dissolved in distilled water (500 mL), and the liquid was adjusted to pH 11 by adding a 1 M aqueous solution of sodium hydroxide. Distilled water was added to the solution to adjust the final liquid volume to 1000 mL, and sodium chloride (50 g) was added. This solution was passed through a column of adsorbent resin HP-20ss (manufactured by Mitsubishi Chemical Corp., 250 mL), washed with a 5% aqueous solution of sodium chloride (1000 mL) and distilled water (1000 mL), and eluted with a 50% aqueous solution of acetonitrile (1250 mL). The eluted fraction including the target product was eluted by passing through a column of a cation exchange resin Dowex 50W (proton type, 150 mL), and was further eluted with a 50% aqueous solution of acetonitrile (150 mL). The eluted fraction including the target product was concentrated under reduced pressure until the liquid volume reached about 150 mL, and then freeze-dried, to obtain the title compound (8.30 g).

The average polymerization number of glutamic acid (the number of carboxylic acids) per molecule of the subject compound, based on the titration value obtained by using an aqueous solution of sodium hydroxide, was 26.72.

Reference Example 2

Synthesis of N-acetylation Product of Block Copolymer of Monomethoxypolyethylene Glycol Having Molecular Weight of about 12000 and Polyglutamic Acid Having a Polymerization Number of about 17.5

The title compound was obtained according to the method described in Reference Example 1, by using 21 equivalents of BLG-NCA relative to the polyethylene glycol.

The average degree of polymerization of glutamic acid (number of carboxylic acids) per molecule of the subject compound, based on the titration value obtained by using an aqueous solution of sodium hydroxide, was 17.47.

Reference Example 3

Synthesis of N-acetylation Product of Block Copolymer of Monomethoxypolyethylene Glycol Having Molecular Weight of about 12000 and Polyglutamic Acid Having a Polymerization Number of about 22

The title compound was obtained according to the method described in Reference Example 1, by using 25 equivalents of BLG-NCA relative to the polyethylene glycol.

The average polymerization number of glutamic acid (the number of carboxylic acids) per molecule of the subject compound, based on the titration value obtained by using an aqueous solution of sodium hydroxide, was 22.14.

Reference Example 4

Synthesis of N-acetylation Product of Block Copolymer of Monomethoxypolyethylene Glycol Having Molecular Weight of about 12000 and Polyglutamic Acid Having Degree of Polymerization of about 26

The title compound was obtained according to the method described in Reference Example 1, by using 30 equivalents of BLG-NCA relative to the polyethylene glycol.

The average polymerization number of glutamic acid (the number of carboxylic acids) per molecule of the subject compound, based on the titration value obtained by using an aqueous solution of sodium hydroxide, was 25.85.

Example 1

Synthesis of Amide Conjugate of N-acetylation Product of Block Copolymer of Monomethoxypolyethylene Glycol Having Molecular Weight of about 12000 and Polyglutamic Acid Having a Polymerization Number of about 26, with L-phenylalanine Benzyl Ester (about 85% with Respect to Carboxyl Groups of Polycarboxylic Acid)

The N-acetylation product of a block copolymer of monomethoxypolyethylene glycol having a molecular weight of about 12000 and polyglutamic acid having a polymerization number of about 26 as described in Reference Example 1 (1.28 g), L-phenylalanine benzyl ester hydrochloride (966 mg), and N,N-diisopropylethylamine (577 μL) were dissolved in N,N-dimethylformamide (30 mL), DMT-MM (1.22 g) was added thereto, and the mixture was stirred overnight at 40° C. The reaction liquid was cooled to room temperature, and then was added dropwise to a mixed solvent of diisopropyl ether-ethanol (4:1, 300 mL). After stirring the mixture for 30 minutes, a precipitate separated out therefrom was collected by filtration, and was washed with a mixed solvent of diisopropyl ether-ethanol (4:1), to obtain the title compound (1.60 g).

The subject compound was hydrolyzed, and then the benzyl alcohol liberated therefrom was quantified by high performance liquid chromatography (HPLC), to thereby determine the binding ratio of the Phe-OBzl group bound to the subject compound via an amide linkage. The binding ratio was 84.5% with respect to the carboxyl groups of the polyglutamic acid.

Method of Hydrolysis

The title compound (10.58 mg) was dissolved in methanol (1.0 mL), a 0.5 M aqueous solution of sodium hydroxide (1.0 mL) was added thereto, and the mixture was stirred for 1 hour at 40° C. The mixture was neutralized with acetic acid, and was diluted with distilled water, to obtain precisely 10 mL of the solution.

Analysis Conditions for HPLC (Analysis of Benzyl Alcohol)

Column: YMC Hydrosphere, 4.6φ×250 mm;
Column temperature: 40° C.;
Eluent liquid A: 1% aqueous solution of phosphoric acid, liquid B: acetonitrile;
Gradient: liquid B % (time, minutes) 0(0), 0(5), 80(25), 80(35), stop(35.01);
Flow rate: 1 mL/min;
Detector (detection wavelength): UV (210 nm)

Example 2

Synthesis of Amide Conjugate of N-acetylation Product of Block Copolymer of Monomethoxypolyethylene Glycol Having Average Molecular Weight of about 12000 and Polyglutamic Acid Having a Polymerization Number of 26.72, with L-phenylalanine (about 85% with Respect to Carboxyl Groups of Polyglutamic Acid)

The compound synthesized in Example 1 (1.60 g) was dissolved in N,N-dimethylformamide (30 mL), 5% palladium-carbon (water content 55%, 150 mg) was added thereto, and the mixture was stirred overnight at room temperature in a hydrogen atmosphere. The palladium-carbon was separated by filtration, subsequently the filtrate was added dropwise to a mixed solvent of isopropyl ether-ethyl acetate (4:1, 300 mL) under stirring, and the mixture was stirred for another one hour. A precipitate separated out therefrom was collected by filtration, and was washed with a mixed solvent of diisopropyl ether-ethyl acetate (4:1). The obtained product was dissolved in a 50% aqueous solution of acetonitrile, a cation exchange resin Dowex 50W (proton type, 2 mL) was added thereto, and the mixture was shaken at room temperature for 2 hours. The resin was removed by filtration, and the resin was washed with a 50% aqueous solution of acetonitrile. The resulting filtrate was concentrated under reduced pressure to a half the volume, and then was freeze-dried, to obtain the title compound (1.42 g).

The subject compound was hydrolyzed by the same method as in Example 1, and then the benzyl alcohol liberated therefrom was quantified by high performance liquid chromatography (HPLC) under the same conditions as in Example 1. Thereby, it was confirmed that benzyl alcohol was not detected.

Example 3

High Molecular Weight Derivative of Nucleic Acid Antimetabolite of Formula (1) in which R is Methyl Group, A is Acetyl Group, Average Value of N is 272, Average Value of a+b is 26.72, Average Value of a is 22.6, Average Value of b is 4.1, X is Phenylalanine Residue, Y is Hydroxyl Group, Isopropylaminocarbonylisopropylamino Group and Gemcitabine Residue To the compound synthesized in Example 2 (704 mg) and gemcitabine hydrochloride (300 mg), N,N-dimethylformamide (15 mL) and N,N-diisopropylethylamine (174 μL) were added, and the mixture was stirred at 40° C. After dissolving the compounds, 4-dimethylaminopyridine (24.4 mg) and diisopropylcarbodiimide (313 μL) were added thereto, and the resulting mixture was stirred overnight at 40° C. The reaction liquid was cooled to room temperature, and then was added dropwise to a mixed solvent of diisopropyl ether-ethanol (4:1, 150 mL). After stirring the mixture for 30 minutes, a precipitate separated out therefrom was collected by filtration, and was washed with a mixed solvent of diisopropyl ether-ethanol (4:1). The obtained product was dissolved in a 50% aqueous solution of acetonitrile, a cation exchange resin Dowex 50W (proton type, 2 mL) was added thereto, and the mixture was shaken at room temperature for 2 hours. The resin was removed by filtration, and the resin was washed with a 50% aqueous solution of acetonitrile. The obtained filtrate was concentrated under reduced pressure to a half the volume, and then was freeze-dried, to obtain the title compound (720 mg).

The subject compound was hydrolyzed, and then the gemcitabine liberated therefrom was quantified by high performance liquid chromatography (HPLC) to determine the gemcitabine content in the subject compound, which was 10.9% (w/w) in terms of gemcitabine hydrochloride. The compound of the present invention was also analyzed by HPLC, and the content of free gemcitabine was 0.2% or less.

Method of Hydrolysis

The title compound (11.71 mg) was dissolved in methanol (1.0 mL), a 0.5 M aqueous solution of sodium hydroxide (1.0 mL) was added thereto, and the mixture was stirred for 1 hour at 40° C. The mixture was neutralized with acetic acid, and then was diluted with distilled water, to obtain precisely 10 mL of the solution.

Analysis Conditions for HPLC (Analysis of Gemcitabine)
Column: YMC Hydrosphere, 4.6φ×250 mm;
Column temperature: 40° C.;
Eluent liquid A: 1% aqueous solution of phosphoric acid, liquid B: acetonitrile;
Gradient: liquid B % (time, minutes) 0(0), 0(5), 80(25), 80(35), stop(35.01);
Flow rate: 1 mL/min;
Detector (detection wavelength): UV (210 nm)

Furthermore, the molar ratio of the isopropylaminocarbonylisopropylamino group with respect to gemcitabine in the subject compound was determined from the $^1$H-NMR (proton nuclear magnetic resonance spectroscopy) spectrum of a solution of the compound in deuterated sodium hydroxide/deuterated water/deuterated acetonitrile, and the value was 0.24.

Example 4

High Molecular Weight Derivative of Nucleic Acid Antimetabolite of Formula (1) in which R is Methyl Group, A is Acetyl Group, Average Value of n is 272, Average Value of a+b is 26.72, Average Value of a is 22.6, Average Value of b is 4.1, X is Phenylalanine Residue, Y is Hydroxyl Group, Isopropylaminocarbonylisopropylamino Group and Doxifluridine Residue The compound synthesized in Example 2 (704 mg) and doxifluridine (246 mg) were added to N,N-dimethylformamide (15 mL), and the mixture was stirred at 40° C. After dissolving the compounds, 4-dimethylaminopyridine (24.4 mg) and diisopropylcarbodiimide (313 μL) were added thereto, and the resulting mixture was stirred overnight at 40° C. The reaction liquid was cooled to room temperature, and then was added dropwise to a mixed solvent of diisopropyl ether-ethanol (4:1, 150 mL). After stirring the mixture for 30 minutes, a precipitate separated out therefrom was collected by filtration, and was washed with a mixed solvent of diisopropyl ether-ethanol (4:1). The obtained product was dissolved in a 50% aqueous solution of acetonitrile, a cation exchange resin Dowex 50W (proton type, 2 mL) was added thereto, and the mixture was shaken at room temperature for 2 hours. The resin was removed by filtration, and the resin was washed with a 50% aqueous solution of acetonitrile. The obtained filtrate was concentrated under reduced pressure to a half of the volume, and then was freeze-dried, to obtain the title compound (720 mg).

The subject compound was hydrolyzed, and then the doxifluridine liberated therefrom was quantified by high performance liquid chromatography (HPLC) to determine the doxifluridine content in the subject compound, which was 7.95% (w/w) in terms of doxifluridine hydrochloride. The compound of the present invention was also analyzed by HPLC, and the content of free doxifluridine was 0.2% or less.

Method of Hydrolysis

The title compound (11.57 mg) was dissolved in methanol (1.0 mL), a 0.5 M aqueous solution of sodium hydroxide (1.0 mL) was added thereto, and the mixture was stirred for 1 hour at 40° C. The mixture was neutralized with acetic acid, and then was diluted with distilled water, to obtain precisely 10 mL of the solution.

Analysis Conditions for HPLC (Analysis of Doxifluridine)
Column: YMC Hydrosphere, 4.6φ×250 mm;
Column temperature: 40° C.;

Eluent liquid A: 1% aqueous solution of phosphoric acid, liquid B: acetonitrile;

Gradient: liquid B % (time, minutes) 0(0), 0(5), 80(25), 80(35), stop(35.01);

Flow rate: 1 mL/min;

Detector (detection wavelength): UV (210 nm)

Furthermore, the molar ratio of the isopropylaminocarbonylisopropylamino group with respect to doxifluridine in the subject compound was determined from the $^1$H-NMR (proton nuclear magnetic resonance spectroscopy) spectrum of a solution of the compound in deuterated sodium hydroxide/deuterated water/deuterated acetonitrile, and the value was 0.37.

Example 5

Synthesis of Amide Conjugate of N-acetylation Product of Block Copolymer of Monomethoxypolyethylene Glycol Having Molecular Weight of about 12000 and Polyaspartic Acid Having a Polymerization Number of about 36, with L-phenylalanine Benzyl Ester (about 96% with Respect to Carboxyl Groups of Polycarboxylic Acid)

The N-acetylation product of a block copolymer of monomethoxypolyethylene glycol-polyaspartic acid produced according to the method described in Patent Document 3 (a polymerization number of aspartic acid, 35.7; 1.0 g), L-phenylalanine benzyl ester hydrochloride (968 mg), and N,N-diisopropylethylamine (578 µL) were dissolved in N,N-dimethylformamide (15 mL), DMT-MM (1.22 g) was added thereto, and the mixture was stirred overnight at room temperature. The reaction liquid was cooled to room temperature, and then was added dropwise to a mixed solvent of diisopropyl ether-ethanol (4:1, 200 mL). After stirring the mixture for 30 minutes, a precipitate separated out there from was collected by filtration, and was washed with a mixed solvent of diisopropyl ether-ethanol (4:1), to obtain the title compound (1.39 g).

The subject compound was hydrolyzed by the same method as in Example 1, and then the benzyl alcohol liberated therefrom was quantified by high performance liquid chromatography (HPLC) under the same conditions as in Example 1, to thereby determine the binding ratio of the Phe-OBzl group bound to the subject compound via an amide linkage. The binding ratio was 95.8% with respect to the carboxyl groups of the polyglutamic acid.

Example 6

Synthesis of Amide Conjugate of N-acetylation Product of Block Copolymer of Monomethoxypolyethylene Glycol Having Molecular Weight of about 12000 and Polyaspartic Acid Having a Polymerization Number of about 36, with L-phenylalanine (about 96% with Respect to Carboxyl Groups of Polycarboxylic Acid)

The compound synthesized in Example 5 (1.39 g) was dissolved in N,N-dimethylformamide (25 mL), 5% palladium-carbon (water content 55%, 140 mg) was added thereto, and the mixture was stirred overnight at room temperature in a hydrogen atmosphere. The palladium-carbon was separated by filtration, and then the filtrate was added dropwise to a mixed solvent of isopropylether-ethylacetate (4:1, 250 mL) under stirring. The resulting mixture was stirred for another one hour. A precipitate separated out therefrom was collected by filtration, and was washed with a mixed solvent of isopropyl ether-ethyl acetate (4:1). The obtained product was dissolved in a 50% aqueous solution of acetonitrile, a cation exchange resin Dowex 50W (proton type, 5 mL) was added thereto, and the mixture was shaken at room temperature for 2 hours. The resin was removed by filtration, and the resin was washed with a 50% aqueous solution of acetonitrile. The obtained filtrate was concentrated under reduced pressure to a half the volume, and then was freeze-dried, to obtain the title compound (0.99 g).

The subject compound was hydrolyzed by the same method as in Example 1, and then the benzyl alcohol liberated therefrom was quantified by high performance liquid chromatography (HPLC) under the same conditions as in Example 1. Thereby, it was confirmed that benzyl alcohol was not detected.

Example 7

High Molecular Weight Derivative of Nucleic Acid Antimetabolite of Formula (4) in which R is Methyl Group, A is Acetyl Group, Average Value of n is 272, Average Value of c+d+e+f+g is 35.7, Average Value of c+d is 34.2, Average Value of e+f+g is 1.5, X is Phenylalanine Residue, Y is Hydroxyl Group, Isopropylaminocarbonylisopropylamino Group and Gemcitabine Residue To the compound synthesized in Example 6 (531 mg) and gemcitabine hydrochloride (269 mg), N,N-dimethylformamide (10 mL) and N,N-diisopropylethylamine (156 µL) were added, and the mixture was stirred at 40° C. After 30 minutes, 4-dimethylaminopyridine (21.9 mg) and diisopropylcarbodiimide (281 L) were added thereto, and the resulting mixture was stirred overnight at 40° C. The reaction liquid was cooled to room temperature, and then was added dropwise to a mixed solvent of diisopropyl ether-ethanol (4:1, 100 mL). After stirring the mixture for 30 minutes, a precipitate separated out therefrom was collected by filtration, and was washed with a mixed solvent of diisopropyl ether-ethanol (4:1). The obtained product was dissolved in a 50% aqueous solution of acetonitrile, and the solution was dialyzed in distilled water (2 L×3) using a dialysis membrane (fractionation molecular weight: 12000 to 14000). The dialyzed solution was freeze-dried, and the title compound (491 mg) was obtained by the freeze-drying.

The subject compound (18.46 mg) was hydrolyzed by the same method as in Example 3, and then the gemcitabine liberated therefrom was quantified by high performance liquid chromatography (HPLC) under the same conditions as in Example 3, to determine the gemcitabine content in the subject compound, which was 19.2% (w/w) in terms of gemcitabine hydrochloride. The compound of the present invention was also analyzed by HPLC, and the content of free gemcitabine was 0.2% or less.

Furthermore, the molar ratio of the isopropylaminocarbonylisopropylamino group with respect to gemcitabine in the subject compound was determined from the $^1$H-NMR (proton nuclear magnetic resonance spectroscopy) spectrum of a solution of the compound in deuterated sodium hydroxide/deuterated water/deuterated acetonitrile, and the value was 0.23.

Example 8

High Molecular Weight Derivative of Nucleic Acid Antimetabolite of Formula (4) in which R is Methyl Group, A is Acetyl Group, Average Value of n is 272, Average Value of c+d+e+f+g is 35.7, Average Value of c+d is 34.2, Average Value of e+f+g is 1.5, X is Phenylalanine Residue, Y is Hydroxyl Group and Gemcitabine Residue To the compound synthesized in Example 6 (500 mg) and gemcitabine hydrochloride (253 mg), N,N-dimethylformamide (10 mL) and N,N-diisopropylethylamine (147 µL) were added, and the mixture was stirred at 40° C. After 30 minutes, 2-ethoxy-1-ethoxycarbonyl-1,2-dihydroquinoline (EEDQ, 261 mg) was added thereto, and the resulting mixture was stirred overnight at 40° C. The reaction liquid was cooled to room temperature, and then was added dropwise to a mixed solvent of diisopropyl ether-ethanol (4:1, 100 mL). After stirring the mixture for 30 minutes, a precipitate separated out therefrom was collected by filtration, and was washed with a mixed solvent of diisopropyl ether-ethanol (4:1). The obtained product was dissolved in a 50% aqueous solution of acetonitrile, and the solution was dialyzed in distilled water (2 L×3) using a dialysis membrane (molecular weight cut off: 12000 to 14000). The dialyzed solution was freeze-dried, and the title compound (513 mg) was obtained by the freeze-drying.

The subject compound (14.93 mg) was hydrolyzed by the same method as in Example 3, and then the gemcitabine liberated therefrom was quantified by high performance liquid chromatography (HPLC) under the same conditions as in Example 3, to determine the gemcitabine content in the subject compound, which was 13.2% (w/w) in terms of gemcitabine hydrochloride. The compound of the present invention was also analyzed by HPLC, and the content of free gemcitabine was 0.2% or less.

Here, since 2-ethoxy-1-ethoxycarbonyl-1,2-dihydroquinoline (EEDQ) was used as the condensing agent in this reaction, the group —N(R1)CONH(R2) was not verified by $^1$H-NMR.

Example 9

Synthesis of Amide Conjugate of N-acetylation Product of Block Copolymer of Monomethoxypolyethylene Glycol Having Molecular Weight of about 12000 and Polyglutamic Acid Having a Polymerization Number of about 17.5, with L-phenylalanine Benzyl Ester (about 100% with Respect to Carboxyl Groups of Polycarboxylic Acid)

The N-acetylation product of a block copolymer of monomethoxypolyethylene glycol having a molecular weight of about 12000 and polyglutamic acid having a polymerization number of about 17.5 synthesized in Reference Example 2 (1.80 g), L-phenylalanine benzyl ester hydrochloride (963 mg), and N,N-diisopropylethylamine (575 µL) were dissolved in N,N-dimethylformamide (36 mL), DMT-MM (1.22 g) was added thereto, and the mixture was stirred overnight at 40° C. The reaction liquid was cooled to room temperature, and then was added dropwise to a mixed solvent of diisopropyl ether-ethanol (4:1, 400 mL). After stirring the mixture for 30 minutes, a precipitate separated out therefrom was collected by filtration, and was washed with a mixed solvent of diisopropyl ether-ethanol (4:1), to obtain the title compound (2.42 g).

The subject compound was hydrolyzed by the same method as in Example 1, and then the benzyl alcohol liberated therefrom was quantified by high performance liquid chromatography (HPLC) under the same conditions as in Example 1, to thereby determine the binding ratio of the Phe-OBzl group bound to the subject compound via an amide linkage. The binding ratio was 100.2% with respect to the carboxyl groups of the polyglutamic acid.

Example 10

Synthesis of Amide Conjugate of N-acetylation Product of Block Copolymer of Monomethoxypolyethylene Glycol Having Molecular Weight of about 12000 and Polyglutamic Acid Having a Polymerization Number of about 17.5, with L-phenylalanine (about 100% with Respect to Carboxyl Groups of Polycarboxylic Acid)

The compound synthesized in Example 9 (2.40 g) was dissolved in N,N-dimethylformamide (48 mL), 5% palladium-carbon (water content 55%, 240 mg) was added thereto, and the mixture was stirred overnight at room temperature in a hydrogen atmosphere. The palladium-carbon was separated by filtration, subsequently the filtrate was added dropwise to a mixed solvent of isopropyl ether-ethyl acetate (4:1, 500 mL) under stirring, and the mixture was stirred for another one hour. A precipitate separated out therefrom was collected by filtration, and was washed with a mixed solvent of diisopropyl ether-ethyl acetate (4:1). The obtained product was dissolved in a 50% aqueous solution of acetonitrile, a cation exchange resin Muromac C1002 (proton type, Muromachi Technos Co., Ltd., 6 mL) was added thereto, and the mixture was shaken for 2 hours at room temperature. Subsequently, the resin was removed by filtration, and the resin was washed with a 50% aqueous solution of acetonitrile. The obtained filtrate was concentrated under reduced pressure to a half of the volume, and then was freeze-dried, to obtain the title compound (1.96 g).

The subject compound was hydrolyzed by the same method as in Example 1, and then the benzyl alcohol liberated therefrom was quantified by high performance liquid chromatography (HPLC) under the same conditions as in Example 1. Thereby, it was confirmed that benzyl alcohol was not detected.

Example 11

High Molecular Weight Derivative of Nucleic Acid Antimetabolite of Formula (1) in which R is Methyl Group, A is Acetyl Group, Average Value of n is 272, Average Value of a+b is 17.5, Average Value of a is 17.5, Average Value of b is 0, X is Phenylalanine Residue, Y is Hydroxyl Group, Isopropylaminocarbonylisopropylamino Group and Gemcitabine Residue To the compound synthesized in Example 10 (1.83 g), gemcitabine hydrochloride (569 mg) and 4-dimethylaminopyridine (46.4 mg), N,N-dimethylformamide (37 mL) and N,N-diisopropylethylamine (331 µL) were added, and the mixture was stirred at 40° C. After 30 minutes, diisopropylcarbodiimide (595 µL) was added thereto, and the resulting mixture was stirred overnight at 40° C. The reaction liquid was cooled to room temperature, and then was added dropwise to a mixed solvent of diisopropyl ether-ethanol (4:1, 500 mL). After stirring the mixture for 30 minutes, a precipitate separated out therefrom was collected by filtration, and was washed with a mixed solvent of diisopropyl ether-ethanol (4:1). The obtained product was dissolved in a 50% aqueous solution of acetonitrile, a cation exchange resin Muromac C1002 (proton type, Muromachi Technos Co., Ltd., 6 mL) was added thereto, and the mixture was shaken for 2 hours at room temperature. Subsequently, the resin was removed by filtration, and the resin was washed with a 50% aqueous solution of acetonitrile. To approximately a half of the amount of the obtained filtrate, an anion exchange resin Muromac A203T (OH type, Muromachi Technos Co., Ltd., 3 mL) was further added, and the mixture was shaken for 2 hours at room temperature. Subsequently, the resin was removed by filtration, and the resin was washed with a 50% aqueous solution of acetonitrile. The product was concentrated under reduced pressure to a half the volume, and then was freeze-dried, to obtain the title compound (0.93 g).

The subject compound (11.48 mg) was hydrolyzed by the same method as in Example 3, and then the gemcitabine liberated therefrom was quantified by high performance liquid chromatography (HPLC) under the same conditions as in Example 3, to determine the gemcitabine content in the subject compound, which was 9.26% (w/w) in terms of gemcitabine hydrochloride. The compound of the present invention was also analyzed by HPLC, and the content of free gemcitabine was 0.2% or less.

Furthermore, the molar ratio of the isopropylaminocarbonylisopropylamino group with respect to one molecule of gemcitabine in the subject compound was determined from the $^1$H-NMR (proton nuclear magnetic resonance spectroscopy) spectrum of a solution of the compound in deuterated sodium hydroxide/deuterated water/deuterated acetonitrile, and the value was 0.45.

Since the content of gemcitabine hydrochloride, and the molar ratio of the isopropylaminocarbonylisopropylamino group with respect to gemcitabine were obtained, the molar ratio of the hydroxyl group with respect to gemcitabine can be calculated to be 1.5, when it is assumed that phenylalanine was introduced 100% as X (a+b=a).

Example 12

Synthesis of Amide Conjugate of N-acetylation Product of Block Copolymer of Monomethoxypolyethylene Glycol Having Molecular Weight of about 12000 and Polyglutamic Acid Having a Polymerization Number of about 22, with L-phenylalanine Benzyl Ester (about 100% with Respect to Carboxyl Groups of Polycarboxylic Acid)

The N-acetylation product of a block copolymer of monomethoxypolyethylene glycol having a molecular weight of about 12000 and polyglutamic acid having a polymerization number of about 22 synthesized in Reference Example 3 (1.30 g), L-phenylalanine benzyl ester hydrochloride (845 mg), and N,N-diisopropylethylamine (505 μL) were dissolved in N,N-dimethylformamide (26 mL), DMT-MM (1.07 g) was added thereto, and the mixture was stirred overnight at 40° C. The reaction liquid was cooled to room temperature, and then was added dropwise to a mixed solvent of diisopropyl ether-ethanol (4:1, 300 mL). After stirring the mixture for 30 minutes, a precipitate separated out therefrom was collected by filtration, and was washed with a mixed solvent of diisopropyl ether-ethanol (4:1), to obtain the title compound (1.75 g).

The subject compound was hydrolyzed by the same method as in Example 1, and then the benzyl alcohol liberated therefrom was quantified by high performance liquid chromatography (HPLC) under the same conditions as in Example 1, to thereby determine the binding ratio of the Phe-OBzl group bound to the subject compound via an amide linkage. The binding ratio was 99.9% with respect to the carboxyl groups of the polyglutamic acid.

Example 13

Synthesis of Amide Conjugate of N-acetylation Product of Block Copolymer of Monomethoxypolyethylene Glycol Having Molecular Weight of about 12000 and Polyglutamic Acid Having a Polymerization Number of about 22, with L-Phenylalanine (about 100% with Respect to Carboxyl Groups of Polycarboxylic Acid)

The compound synthesized in Example 12 (1.70 g) was dissolved in N,N-dimethylformamide (34 mL), 5% palladium-carbon (water content 55%, 170 mg) was added thereto, and the mixture was stirred overnight at room temperature in a hydrogen atmosphere. The palladium-carbon was separated by filtration, and then the filtrate was added dropwise to a mixed solvent of isopropyl ether-ethyl acetate (4:1, 400 mL) under stirring. The mixture was stirred for another one hour. A precipitate separated out therefrom was collected by filtration, and was washed with a mixed solvent of isopropyl ether-ethyl acetate (4:1). The obtained product was dissolved in a 50% aqueous solution of acetonitrile, a cation exchange resin Muromac C1002 (proton type, Muromachi Technos Co., Ltd., 6 mL) was added thereto, and the mixture was shaken for 2 hours at room temperature. Subsequently, the resin was removed by filtration, and the resin was washed with a 50% aqueous solution of acetonitrile. The obtained filtrate was concentrated under reduced pressure to a half of the volume, and then was freeze-dried, to obtain the title compound (1.42 g).

The subject compound was hydrolyzed by the same method as in Example 1, and then the benzyl alcohol liberated therefrom was quantified by high performance liquid chromatography (HPLC) under the same conditions as in Example 1. Thereby, it was confirmed that benzyl alcohol was not detected.

Example 14

High Molecular Weight Derivative of Nucleic Acid Antimetabolite of Formula (1) in which R is Methyl Group, A is Acetyl Group, Average Value of a is 272, Average Value of a+b is 22.1, Average Value of a is 22.1, Average Value of b is 0, X is Phenylalanine Residue, Y is Hydroxyl Group, Isopropylaminocarbonylisopropylamino Group and Gemcitabine Residue To the compound synthesized in Example 13 (1.40 g), gemcitabine hydrochloride (512 mg) and 4-dimethylaminopyridine (41.8 mg), N,N-dimethylformamide (28 mL) and N,N-diisopropylethylamine (298 μL) were added, and the mixture was stirred at 40° C. After 30 minutes, diisopropylcarbodiimide (535 μL) was added thereto, and the resulting mixture was stirred overnight at 40° C. The reaction liquid was cooled to room temperature, and then was added dropwise to a mixed solvent of diisopropyl ether-ethanol (4:1, 500 mL). After stirring the mixture for 30 minutes, a precipitate separated out therefrom was collected by filtration, and was washed with a mixed solvent of diisopropyl ether-ethanol (4:1). The obtained product was dissolved in a 50% aqueous solution of acetonitrile, a cation exchange resin Muromac C1002 (proton type, Muromachi Technos Co., Ltd., 6 mL) was added thereto, and the mixture was shaken for 2 hours at room temperature. Subsequently, the resin was removed by filtration, and the resin was washed with a 50% aqueous solution of acetonitrile. To approximately a half of the amount of the obtained filtrate, an anion exchange resin Muromac A203T (OH type, Muromachi Technos Co., Ltd., 3 mL) was further added, and the mixture was shaken for 2 hours at room temperature. Subsequently, the resin was removed by filtration, and the resin was washed with a 50% aqueous solution of acetonitrile. The obtained filtrate was concentrated under reduced pressure to a half the volume, and then was freeze-dried, to obtain the title compound (0.77 g).

The subject compound (11.02 mg) was hydrolyzed by the same method as in Example 3, and then the gemcitabine liberated therefrom was quantified by high performance liquid chromatography (HPLC) under the same conditions as in Example 3, to determine the gemcitabine content in the subject compound, which was 11.09% (w/w) in terms of gemcitabine hydrochloride. The compound of the present invention was also analyzed by HPLC, and the content of free gemcitabine was 0.2% or less.

Furthermore, the molar ratio of the isopropylaminocarbonylisopropylamino group with respect to one molecule of gemcitabine in the subject compound was determined from the $^1$H-NMR (proton nuclear magnetic resonance spectroscopy) spectrum of a solution of the compound in deuterated sodium hydroxide/deuterated water/deuterated acetonitrile, and the value was 0.36.

Since the content of gemcitabine hydrochloride, and the molar ratio of the isopropylaminocarbonylisopropylamino group with respect to gemcitabine were obtained, the molar ratio of the hydroxyl group with respect to gemcitabine can be calculated to be 1.5, when it is assumed that phenylalanine was introduced 100% as X (a+b=a).

Example 15

Synthesis of Amide Conjugate of N-acetylation Product of Block Copolymer of Monomethoxypolyethylene Glycol Having Molecular Weight of about 12000 and Polyglutamic Acid Having a Polymerization Number of about 26, with L-Phenylalanine Benzyl Ester (about 97% with Respect to Carboxyl Groups of Polycarboxylic Acid)

The N-acetylation product of a block copolymer of monomethoxypolyethylene glycol having a molecular weight of about 12000 and polyglutamic acid having a polymerization number of about 26 synthesized in Reference Example 4 (1.00 g), L-phenylalanine benzyl ester hydrochloride (736 mg), and N,N-diisopropylethylamine (439 µL) were dissolved in N,N-dimethylformamide (20 mL), DMT-MM (930 mg) was added thereto, and the mixture was stirred overnight at 40° C. The reaction liquid was cooled to room temperature, and then was added dropwise to a mixed solvent of diisopropyl ether-ethanol (4:1, 200 mL). After stirring the mixture for 30 minutes, a precipitate separated out therefrom was collected by filtration, and was washed with a mixed solvent of diisopropyl ether-ethanol (4:1), to obtain the title compound (1.30 g).

The subject compound was hydrolyzed by the same method as in Example 1, and then the benzyl alcohol liberated therefrom was quantified by high performance liquid chromatography (HPLC) under the same conditions as in Example 1, to thereby determine the binding ratio of the Phe-OBzl group bound to the subject compound via an amide linkage. The binding ratio was 97.2% with respect to the carboxyl groups of the polyglutamic acid.

Example 16

Synthesis of Amide Conjugate of N-acetylation Product of Block Copolymer of Monomethoxypolyethylene Glycol Having Molecular Weight of about 12000 and Polyglutamic Acid Having a Polymerization Number of about 26, with L-Phenylalanine (about 97% with Respect to Carboxyl Groups of Polycarboxylic Acid)

The compound synthesized in Example 15 (1.30 g) was dissolved in N,N-dimethylformamide (25 mL), 5% palladium-carbon (water content 55%, 130 mg) was added thereto, and the mixture was stirred overnight at room temperature in a hydrogen atmosphere. The palladium-carbon was separated by filtration, subsequently the filtrate was added dropwise to a mixed solvent of isopropyl ether-ethyl acetate (4:1, 200 mL) under stirring, and the resulting mixture was stirred for another one hour. A precipitate separated out therefrom was collected by filtration, and was washed with a mixed solvent of isopropyl ether-ethyl acetate (4:1). The obtained product was dissolved in a 50% aqueous solution of acetonitrile, a cation exchange resin Muromac C1002 (proton type, Muromachi Technos Co., Ltd., 5 mL) was added thereto, and the mixture was shaken for 2 hours at room temperature. Subsequently, the resin was removed by filtration, and the resin was washed with a 50% aqueous solution of acetonitrile. The obtained filtrate was concentrated under reduced pressure to a half the volume, and then was freeze-dried, to obtain the title compound (1.10 g).

The subject compound was hydrolyzed by the same method as in Example 1, and then the free benzyl alcohol liberated therefrom was quantified by high performance liquid chromatography (HPLC) under the same conditions as in Example 1. Thereby, it was confirmed that benzyl alcohol was not detected.

Example 17

High Molecular Weight Derivative of Nucleic Acid Antimetabolite of Formula (1) in which R is Methyl Group, A is Acetyl Group, Average Value of n is 272, Average Value of a+b is 25.85, Average Value of a is 25.13, Average Value of b is 0.72, X is Phenylalanine Residue, Y is Hydroxyl Group, Isopropylaminocarbonylisopropylamino Group and Gemcitabine Residue To the compound synthesized in Example 16 (995 mg), gemcitabine hydrochloride (402 mg) and 4-dimethylaminopyridine (32.7 mg), N,N-dimethylformamide (20 mL) and N,N-diisopropylethylamine (234 µL) were added, and the mixture was stirred at 40° C. After 30 minutes, diisopropylcarbodiimide (420 µL) was added thereto, and the mixture was stirred overnight at 40° C. The reaction liquid was cooled to room temperature, and then was added dropwise to a mixed solvent of diisopropyl ether-ethanol (4:1, 200 mL). After stirring the mixture for 30 minutes, a precipitate separated out therefrom was collected by filtration, and was washed with a mixed solvent of diisopropyl ether-ethanol (4:1). The obtained product was dissolved in a 50% aqueous solution of acetonitrile, a cation exchange resin Muromac C1002 (proton type, Muromachi Technos Co., Ltd., 4 mL) was added thereto, and the mixture was shaken for 2 hours at room temperature. Subsequently, the resin was removed by filtration, and the resin was washed with a 50% aqueous solution of acetonitrile. To the obtained filtrate, an anion exchange resin Muromac A203T (OH type, Muromachi Technos Co., Ltd., 4 mL) was further added, and the mixture was shaken for 2 hours at room temperature. Subsequently, the resin was removed by filtration, and the resin was washed with a 50% aqueous solution of acetonitrile. The product was concentrated under reduced pressure to a half of the volume, and then was freeze-dried, to obtain the title compound (950 mg).

The subject compound (11.28 mg) was hydrolyzed by the same method as in Example 3, and then the gemcitabine liberated therefrom was quantified by high performance liquid chromatography (HPLC) under the same conditions as in Example 3, to determine the gemcitabine content in the subject compound, which was 12.76% (w/w) in terms of gemcitabine hydrochloride. The compound of the present invention was also analyzed by HPLC, and the content of free gemcitabine was 0.2% or less.

Furthermore, the molar ratio of the isopropylaminocarbonylisopropylamino group with respect to gemcitabine in the subject compound was determined from the $^1$H-NMR (proton nuclear magnetic resonance spectroscopy) spectrum of a solution of the compound in deuterated sodium hydroxide/deuterated water/deuterated acetonitrile, and the value was 0.35.

Since the content of gemcitabine hydrochloride, and the molar ratio of the isopropylaminocarbonylisopropylamino group with respect to gemcitabine were obtained, the molar ratio of the hydroxyl group with respect to gemcitabine can be calculated to be 1.4, when it is assumed that phenylalanine was introduced 100% as X (a+b=a).

Test Example 1

Drug Release Test in the Absence of Enzyme (1)

The compound of Example 3, the compound of Example 4, the compound of Example 7, or the compound of Example 8 was dissolved in phosphate buffered physiological saline (pH 7.4) to a concentration of 1.0 mg/mL, and the solution was left to stand at a constant temperature of 37° C. The amount of released gemcitabine or doxifluridine was measured over time by HPLC, and the ratio of the amount of released gemcitabine or doxifluridine with respect to the total amount of gemcitabine or doxifluridine in the respective compounds used was determined. The results are presented in FIG. 1. The compounds of the present invention were found to release drugs slowly in the absence of enzymes.

Test Example 2

Drug Release Test in the Absence of Enzyme (2)

The compound of Example 11, the compound of Example 14, or the compound of Example 17 was dissolved in phosphate buffered physiological saline (pH 7.4) to a concentration of 1.0 mg/mL, and the solution was left to stand at a constant temperature of 37° C. The amount of released gemcitabine was measured over time by HPLC, and the ratio of the amount of released gemcitabine with respect to the total amount of gemcitabine in the respective compounds used was determined. The results are presented in FIG. 2. The compounds of the present invention were found to release drugs slowly in the absence of enzymes.

Test Example 3

Drug Release in Mouse Blood Plasma

The compound of Example 11 or the compound of Example 17 was dissolved in phosphate buffered physiological saline (pH 7.4), and subsequently blood plasma collected and prepared from mice was added thereto in a four-fold amount (v/v), and the solution was left to stand at a constant temperature of 37° C. 50 µL each of the solution was sampled over time, and was diluted with a 50% aqueous solution of methanol (450 µL). The dilution was subjected to deproteinization with a membrane filter (pore size 0.45 µm), and then the amount of gemcitabine released from the compound of the present invention was measured over time by HPLC, to determine the ratio of the amount of released gemcitabine with respect to the total amount of gemcitabine in the respective compounds of the present invention. The results are presented in FIG. 3. Since the compounds of the present invention slowly released drugs even in the blood plasma, it was found that the compounds of the invention are compounds which do not depend on the hydrolysis reaction by the enzymes in the blood plasma.

When the results of Test Example 2 and Test Example 3 are compared, the compounds of the present invention have higher drug release rates in the mouse blood plasma, as compared to the case where enzymes are absent, but the difference is small. In this regard, it is thought that since the compounds of the present invention have lower sensitivity to the hydrolysis reaction by enzymes, the compounds remain for a long time as high molecular weight derivatives in the mouse blood plasma, and release drugs for a long time.

Test Example 4

Antitumor Effect Against Tumor-Bearing Mouse (1)

Tumor of mouse colon cancer, Colon26, maintained by subcutaneous subculture in mice, was minced into about 2-mm square blocks, and the blocks were transplanted subcutaneously on the dorsal part of a mouse using a trocar. On the 7$^{th}$ day after tumor transplantation, the compound of Example 5 dissolved in a 5% glucose injection solution and gemcitabine hydrochloride as a control drug dissolved in physiological saline were respectively administered once intravenously at the doses indicated in Table 2. The tumor volumes on the day of initiation of administration and on the 8$^{th}$ day after the initiation of administration were calculated by the following equation, and the relative tumor volumes on the day of initiation of administration and on the 8$^{th}$ day after the initiation of administration were determined. The results are presented in Table 2.

$$\text{Tumor volume (mm}^3) = \frac{[\text{Major axis of tumor (mm)}] \times [\text{Minor axis of tumor (mm)}] \times [\text{Minor axis of tumor (mm)}]}{2}$$

TABLE 2

| Drug | Dose (in terms of gemcitabine hydrochloride) (mg/kg) | Relative tumor volume* |
|---|---|---|
| Untreated | 0 | 10.3 ± 2.9 |
| Compound 1 | 80 | 0.6 ± 0.7 |
|  | 40 | 3.7 ± 1.3 |
| Control drug | 200 | 4.8 ± 1.7 |
|  | 40 | 5.3 ± 1.1 |

*Average relative tumor volume (average ± SD) on the 8$^{th}$ day after the initiation of administration, assuming that the tumor volume on the day of initiation of drug administration is 1.0

From these results, it is clear that when compared with the control drug, gemcitabine hydrochloride, the compounds of the present invention have equal or superior antitumor effects at lower doses.

Test Example 5

Antitumor Effect Against Tumor-Bearing Mouse (2)

A tumor mass of mouse colon cancer, Colon26, which had been subcutaneously subcultured in a mouse was cut into a block having an edge of about 2 mm at each side, and was transplanted under the skin of a mouse using a trocar. On the 7th day after tumor transplantation, the compound of Example 11, the compound of Example 14 and the compound of Example 17, dissolved in a 5% glucose injection solution and gemcitabine hydrochloride as a control drug dissolved in physiological saline were respectively administered once intravenously at the doses indicated in Table 3. The tumor volumes on the day of initiation of administration, and on the 7th day and 26th day after the initiation of administration were calculated by the above-described equation, and the relative tumor volumes on the day of initiation of administration and on the 7th day and 26th day after the initiation of administration were determined. The results are presented in Table 3.

TABLE 3

| Drug | Dose (in terms of gemcitabine hydrochloride) | Relative tumor volume * | Relative tumor volume ** |
|---|---|---|---|
| Untreated | 0 | 11.7 ± 1.9 | |
| Compound of Example 11 | 60 | 0.2 ± 0.1 | 0.02 ± 0.01 |
| Compound of Example 14 | 70 | 0.5 ± 0.2 | 0.04 ± 0.02 |
| Compound of Example 17 | 80 | 0.7 ± 0.6 | 0.7 ± 1.4 |
| Control drug | 160 | 1.5 ± 1.5 | 25.8 ± 36.0 |

\* Average relative tumor volume (average ± SD) on the 7th day after the initiation of administration, assuming that the tumor volume on the day of initiation of drug administration is 1.0
\*\* Average relative tumor volume (average ± SD) on the 26th day after the initiation of administration, assuming that the tumor volume on the day of initiation of drug administration is 1.0
The untreated group has no measurement values because the mice died during the experiment From these results, it is clear that when compared with the control drug, gemcitabine hydrochloride, the compounds of the present invention have strong antitumor effects at lower doses for an extended period of time.

Figure 1:
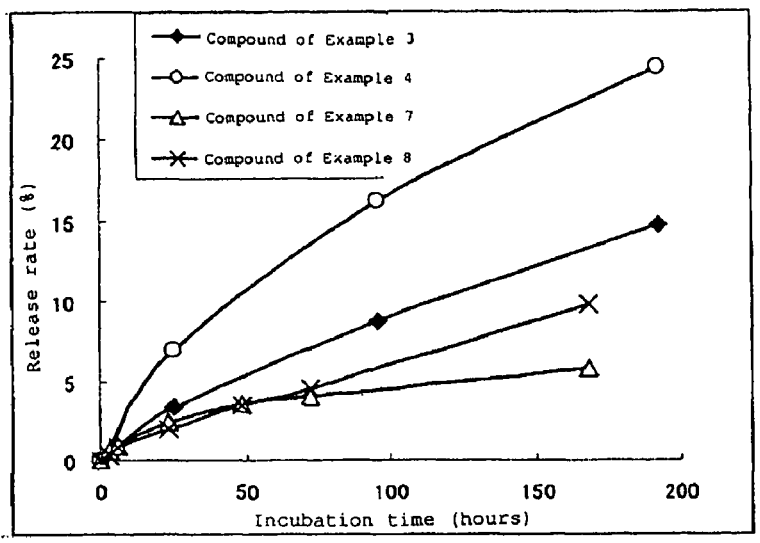
FIG. 1 shows the changes in drug release over time in the absence of enzymes. Symbol ♦ represents the compound of Example 3, ○ represents the compound of Example 4, Δ represents the compound of Example 7, and x represents the compound of Example 8.
Figure 2:
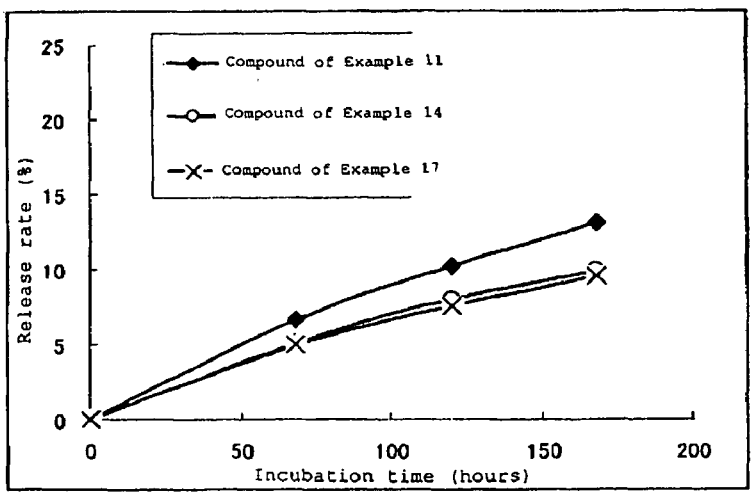
FIG. 2 shows the changes in drug release over time in the absence of enzymes. Symbol ♦ represents the compound of Example 11, ○ represents the compound of Example 14, and x represents the compound of Example 17.
Figure 3:
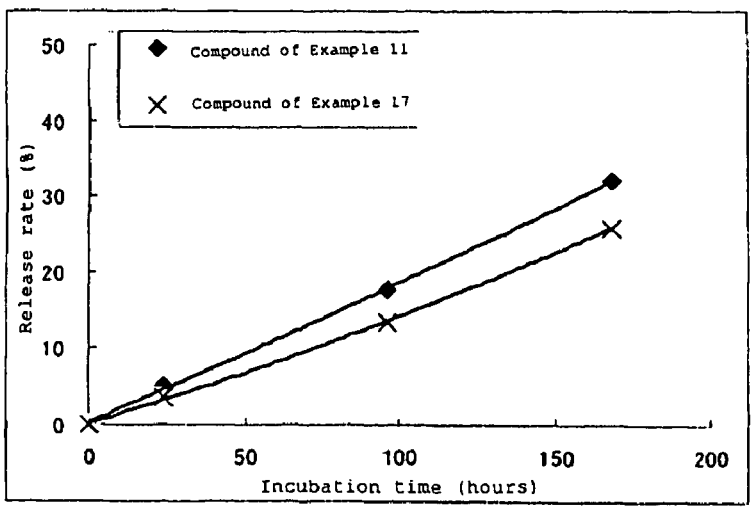
FIG. 3 shows the changes in drug release over time in the mouse blood plasma. Symbol ♦ represents the compound of Example 11, and x represents the compound of Example 17.

The invention claimed is:
1. The high molecular weight derivative of a nucleic acid antimetabolite represented by the following formula (1):

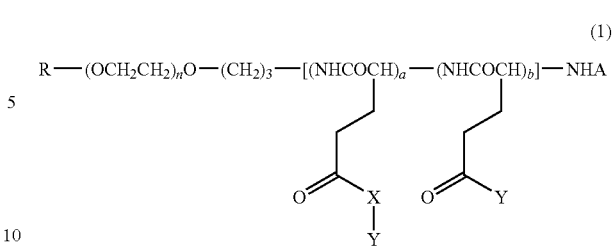

wherein R represents a hydrogen atom or a C1-C6 alkyl group; A represents a hydrogen atom, a C1-C6 acyl group or a C1-C6 alkoxycarbonyl group; a+b represents from 3 to 200 as an average value, while a represents 75 to 100% of a+b, and b represents 0 to 25% of a+b; n represents from 5 to 2000 as an average value; X represents a hydrophobic linker represented by formula (5):

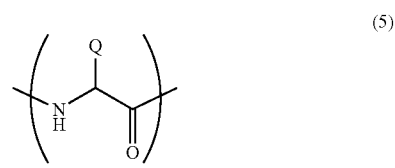

wherein Q represents the side chain of a neutral amino acid; each instance of Y independently represents a group selected from the group consisting of a residue of nucleic acid antimetabolite represented by formula (2):

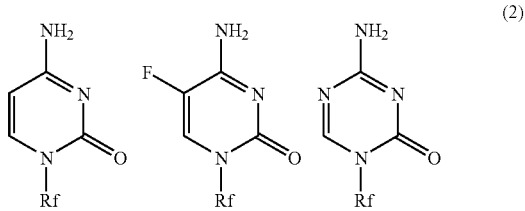

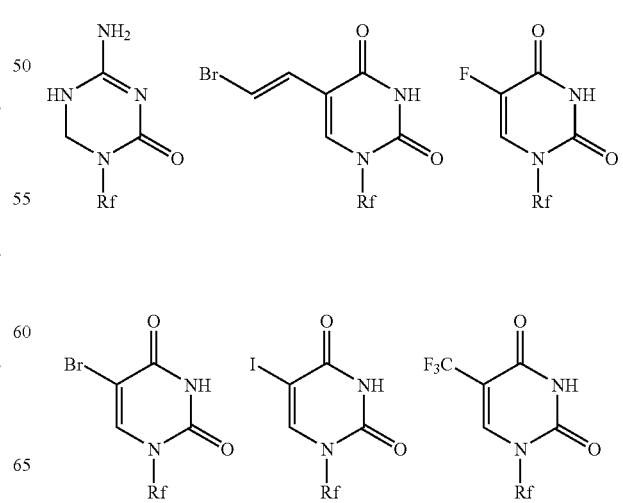

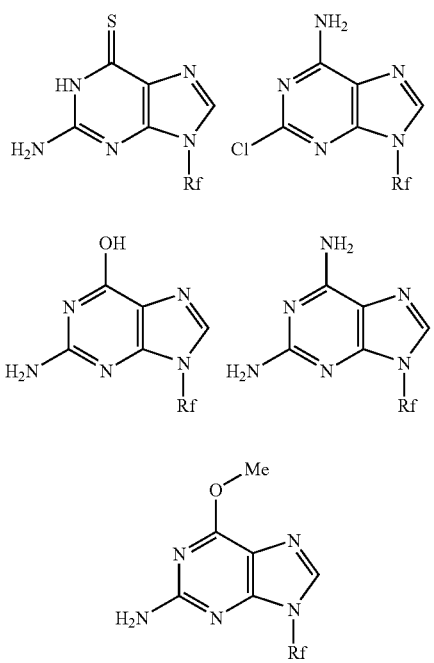

wherein —Rf represents a group selected from the group of substituents of formula (3):

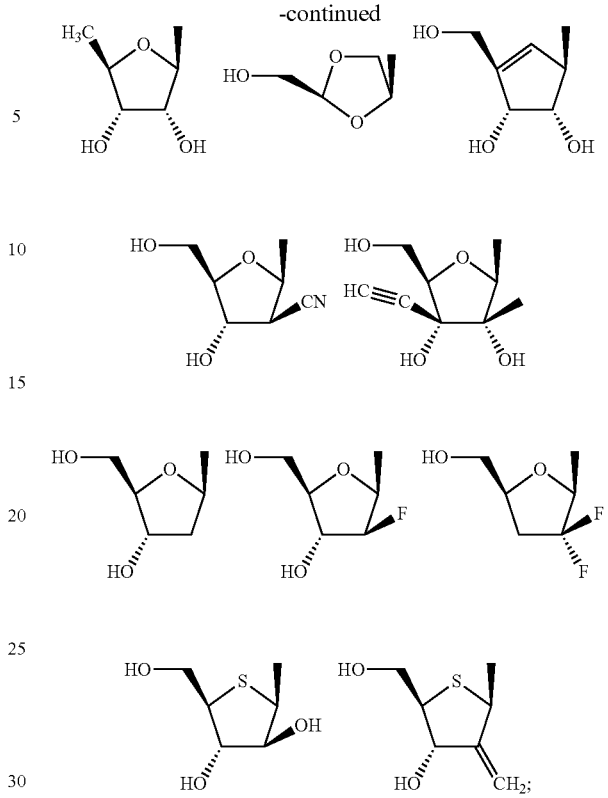

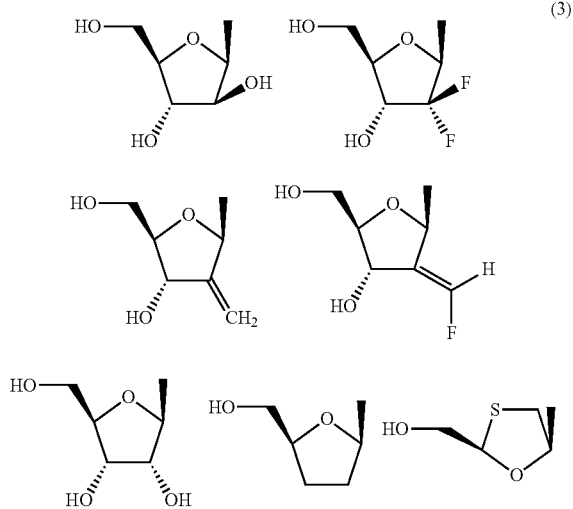

A hydroxyl group, and —N(R1)CONH(R2); wherein the nucleic acid antimetabolite residue is bound by an ester or amide linkage; wherein R1 and R2 may be identical or different, and are each a C1-C6 alkyl group which may be substituted with a tertiary amino group, and wherein, assuming that a+b is 100%, the number of nucleic acid antimetabolite residue is 5 to 80%, the number of —N(R1)CONH(R2) is 0 to 70%, and the number of hydroxyl group is 0 to 70%) and the constituent units of polyglutamic acid are bound in any order.

2. The high molecular weight derivative of a nucleic acid antimetabolite according to claim 1, wherein R is a C1-C4 alkyl group; A is a C2-C4 acyl group; a+b is from 5 to 100 as an average value, wherein a is 80 to 100% of a+b, and b is 0 to 20% of a+b; n is from 50 to 1000 as an average value.

3. The high molecular weight derivative of a nucleic acid antimetabolite according to claim 2, wherein R is a methyl group; A is an acetyl group; a+b is from 10 to 60 as an average value; n is from 100 to 300 as an average value; and the nucleic acid antimetabolite residue is a residue of gemcitabine or doxifluridine.

4. The high molecular weight derivative of a nucleic acid antimetabolite represented by the following formula (4):

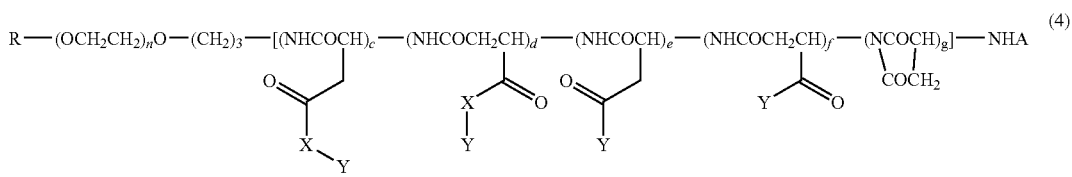

Wherein R represents a hydrogen atom or a C1-C6 alkyl group; A represents a hydrogen atom, a C1-C6 acyl group or a C1-C6 alkoxycarbonyl group; n represents from 5 to 2000 as an average value; X represents a hydrophobic linker represented by formula (5):

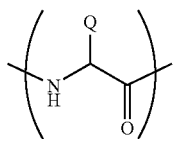
(5)

wherein Q represents the side chain of a neutral amino acid; c+d+e+f+g represents from 3 to 200 as an average value, wherein c+d represents 85 to 100% in c+d+e+f+g, and e+f+g represents 0 to 15% in c+d+e+f+g; each instance of Y independently represents a group selected from the group consisting of a residue of nucleic acid antimetabolite represented by formula (2):

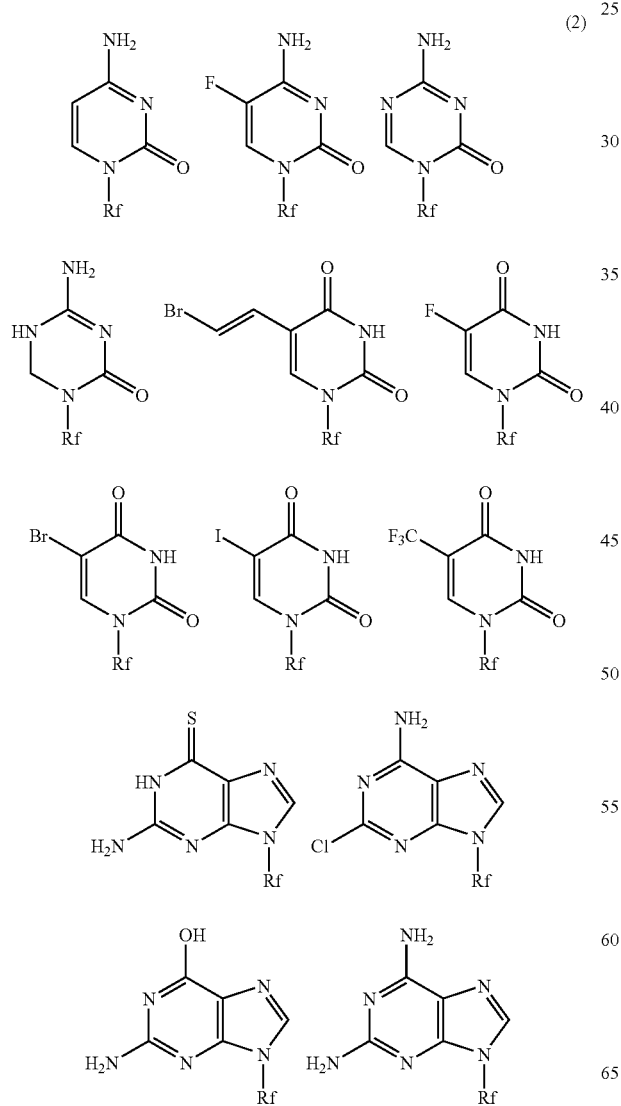
(2)

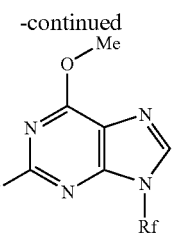

wherein —Rf represents a group selected from the group of substituents of formula (3):

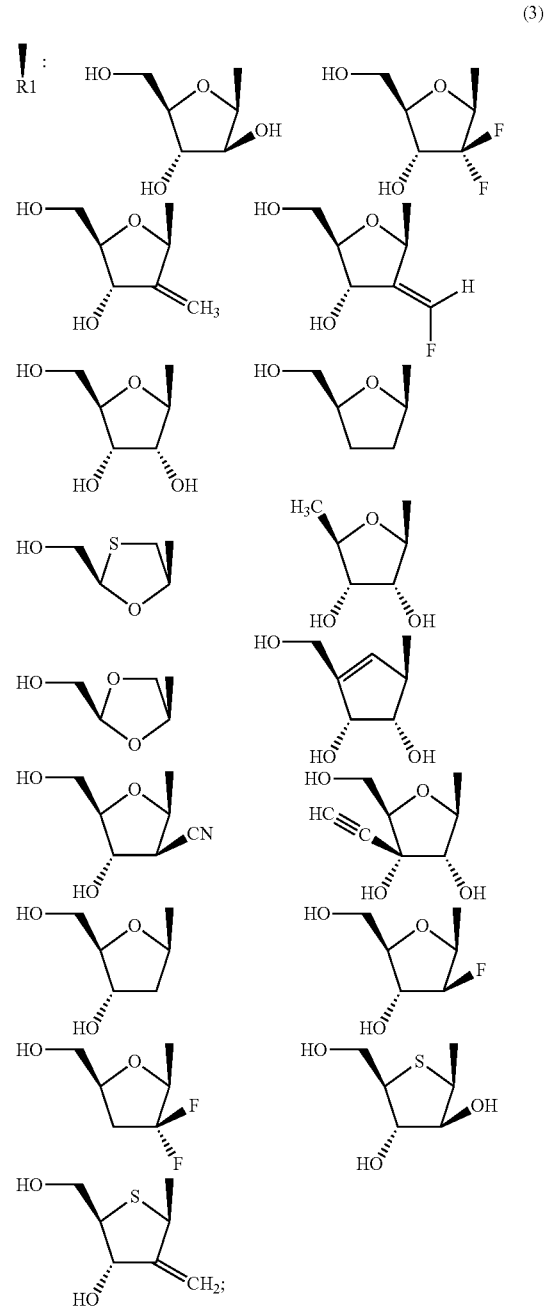
(3)

a hydroxyl group, and —N(R1)CONH(R2); wherein the nucleic acid antimetabolite residue is bound by an ester or amide linkage; wherein R1 and R2 may be identical or different, and are each a C1-C6 alkyl group which may be substituted with a tertiary amino group, wherein, assuming that c+d+e+f+g is 100%, the number of nucleic acid antimetabolite residue is 5 to 80%, the number of —N(R1)CONH(R2) is 0 to 70%, and the number of hydroxyl group is 0 to 70%); and the respective constituent units of polyaspartic acid are bound in any order.

5. The high molecular weight derivative of a nucleic acid antimetabolite according to claim 4, wherein R is a C1-C4 alkyl group; A is a C2-C4 acyl group; c+d+e+f+g is from 5 to 100 as an average value, wherein c+d is 90 to 100% of c+d+e+f+g, and e+f+g is 0 to 10% of c+d+e+f+g; n is from 50 to 1000 as an average value.

6. The high molecular weight derivative of a nucleic acid antimetabolite according to claim 5, wherein R is a methyl group; A is an acetyl group; c+d+e+f+g is from 10 to 60 as an average value; n is from 100 to 300 as an average value; and the nucleic acid antimetabolite residue is a residue of gemcitabine or doxifluridine.

7. The high molecular weight derivative of a nucleic acid antimetabolite according to claim 1, wherein Q is an isopropyl group or a benzyl group.

8. The high molecular weight derivative of a nucleic acid antimetabolite according to claim 1, wherein R is a methyl group; A is an acetyl group; a+b is from 10 to 60 as an average value; n is from 100 to 300 as an average value; the hydrophobic linker is a phenylalanine residue; the nucleic acid antimetabolite residue is a gemcitabine residue; and —N(R1)CONH(R2) is an isopropylaminocarbonylisopropylamino group.

9. The high molecular weight derivative of a nucleic acid antimetabolite according to claim 4, wherein R is a methyl group; A is an acetyl group; c+d+e+f+g is from 10 to 60 as an average value; n is from 100 to 300 as an average value; the hydrophobic linker is a phenylalanine residue; the nucleic acid antimetabolite is a gemcitabine; and —N(R1)CONH(R2) is an isopropylaminocarbonylisopropylamino group.

10. An antitumor agent comprising the high molecular weight derivative of a nucleic acid antimetabolite according to claim 1 or 4 as an active ingredient.

11. An antiviral agent comprising the high molecular weight derivative of a nucleic acid antimetabolite according to claim 1 or 4 as an active ingredient.

12. The method for manufacturing the high molecular weight derivative of a nucleic acid antimetabolite, the method comprising introducing the nucleic acid antimetabolite to a high molecular weight derivative in which a hydrophobic linker is bound to a carboxyl group of a high molecular weight compound and which is represented by formula (6):

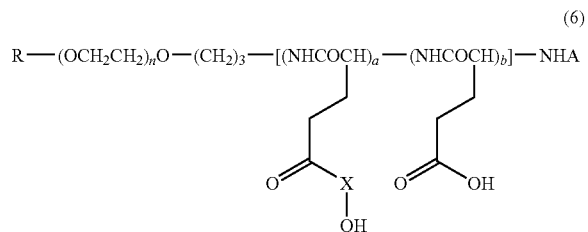

wherein R represents a hydrogen atom or a C1-C6 alkyl group; A represents a hydrogen atom, a C1-C6 acyl group or a C1-C6 alkoxycarbonyl group; a+b represents from 3 to 200 as an average value, while a represents 75 to 100% of a+b, and b represents 0 to 25% of a+b; n represents from 5 to 2000 as an average value; X represents a hydrophobic linker represented by formula (5):

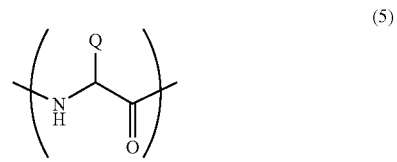

wherein Q represents the side chain of a neutral amino acid.

13. The method for manufacturing the high molecular weight derivative of a nucleic acid antimetabolite, the method comprising introducing the nucleic acid antimetabolite to a high molecular weight derivative in which a hydrophobic linker is bound to a carboxyl group of a high molecular weight compound and which is represented by formula (7):

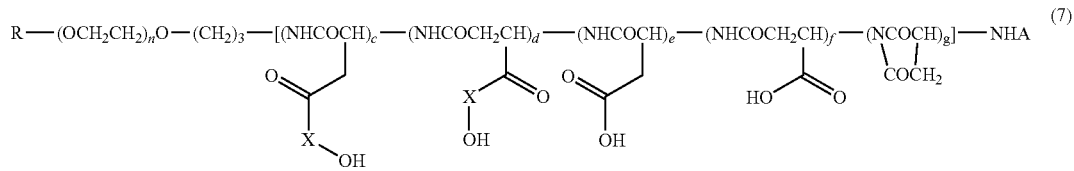

wherein R represents a hydrogen atom or a C1-C6 alkyl group; A represents a hydrogen atom, a C1-C6 acyl group or a C1-C6 alkoxycarbonyl group; n represents from 5 to 2000 as an average value; X represents a hydrophobic linker represented by formula (5):

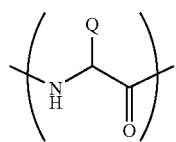

(5)

wherein Q represents the side chain of a neutral amino acid; c+d+e+f+g represents from 3 to 200 as an average value, wherein c+d represents 85 to 100% in c+d+e+f+g, and e+f+g represents 0 to 15% in c+d+e+f+g.

14. A high molecular weight derivative represented by the formula (6) set forth in claim 12, wherein a hydrophobic linker represented by the formula (5):

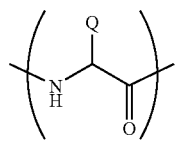

(5)

wherein Q represents a side chain of a neutral amino acid; is bound to a carboxyl group in the side chain of the high molecular weight compound.

15. A high molecular weight derivative represented by the formula (7) set forth in claim 13, wherein a hydrophobic linker represented by formula (5):

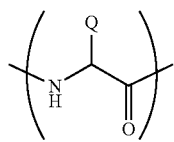

(5)

wherein Q represents the side chain of a neutral amino acid; is bound to a carboxyl group in the side chain of the high molecular weight compound.

16. A high molecular weight derivative according to claim 14, wherein R is a methyl group; A is an acetyl group; a+b is from 10 to 60 as an average value; and n is from 100 to 300 as an average value.

17. A high molecular weight derivative according to claim 15, wherein R is a methyl group; A is an acetyl group; c+d+e+f+g is from 10 to 60 as an average value; and n is from 100 to 300 as an average value.

18. The high molecular weight derivative of a nucleic acid antimetabolite according to claim 4, wherein Q is an isopropyl group or a benzyl group.

* * * * *